(12) United States Patent
Zhang et al.

(10) Patent No.: US 8,741,332 B2
(45) Date of Patent: *Jun. 3, 2014

(54) COMPOSITIONS AND METHODS FOR DERMALLY TREATING NEUROPATHIC PAIN

(75) Inventors: Jie Zhang, Salt Lake City, UT (US); Kevin S. Warner, West Jordan, UT (US); Sanjay Sharma, Sandy, UT (US)

(73) Assignee: Nuvo Research Inc., Mississauga, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 11/640,139

(22) Filed: Dec. 14, 2006

(65) Prior Publication Data

US 2007/0196458 A1   Aug. 23, 2007

Related U.S. Application Data

(63) Continuation-in-part of application No. 11/146,917, filed on Jun. 6, 2005.

(60) Provisional application No. 60/750,637, filed on Dec. 14, 2005, provisional application No. 60/750,519, filed on Dec. 14, 2005, provisional application No. 60/577,536, filed on Jun. 7, 2004.

(51) Int. Cl.
| | |
|---|---|
| *A61F 13/00* | (2006.01) |
| *A61K 9/00* | (2006.01) |
| *A61K 9/70* | (2006.01) |
| *A61L 26/00* | (2006.01) |

(52) U.S. Cl.
CPC ............ *A61K 9/0014* (2013.01); *A61K 9/7015* (2013.01); *A61L 26/0076* (2013.01)
USPC ........................................... 424/443

(58) Field of Classification Search
None
See application file for complete search history.

(56) References Cited

U.S. PATENT DOCUMENTS

| | | |
|---|---|---|
| 4,107,161 A | 8/1978 | Agusti |
| 4,430,325 A | 2/1984 | Gaffar et al. |
| 4,645,502 A | 2/1987 | Gale et al. |
| 4,695,465 A | 9/1987 | Kigasawa et al. |
| 4,780,320 A | 10/1988 | Baker |
| 4,956,171 A | 9/1990 | Chang |
| 5,091,171 A | 2/1992 | Yu et al. |
| 5,183,459 A | 2/1993 | Bernard |
| 5,370,879 A | 12/1994 | Masterson et al. |
| 5,378,730 A | 1/1995 | Lee et al. |
| 5,399,355 A | 3/1995 | Riedl et al. |
| 5,460,820 A | 10/1995 | Ebert et al. |
| 5,589,156 A | 12/1996 | Henry |
| 5,658,583 A | 8/1997 | Zhang et al. |
| 5,707,981 A | 1/1998 | Chriki |
| 5,733,572 A | 3/1998 | Unger et al. |
| 5,741,510 A | 4/1998 | Rolf et al. |
| 5,747,022 A | 5/1998 | Slavtcheff |
| 5,885,597 A | 3/1999 | Botknecht et al. |
| 5,906,814 A | 5/1999 | Epstein |
| 5,955,502 A | 9/1999 | Hansen et al. |
| 6,036,966 A | 3/2000 | Youssefyeh |
| 6,045,814 A | 4/2000 | Roulier et al. |
| 6,143,794 A | 11/2000 | Chaudhuri et al. |
| 6,207,184 B1 | 3/2001 | Ikeda et al. |
| 6,207,703 B1 | 3/2001 | Ponikau |
| 6,211,250 B1 | 4/2001 | Tomlinson et al. |
| 6,221,915 B1 | 4/2001 | McCleane |
| 6,245,347 B1 | 6/2001 | Zhang et al. |
| 6,290,984 B1 | 9/2001 | Tapolsky et al. |
| 6,290,986 B1 | 9/2001 | Murdock et al. |
| 6,324,424 B1 | 11/2001 | Ledger et al. |
| 6,342,537 B1 | 1/2002 | Thomsen et al. |
| 6,387,383 B1 | 5/2002 | Dow et al. |
| 6,391,869 B1 | 5/2002 | Parks et al. |
| 6,395,955 B1 | 5/2002 | Roe et al. |
| 6,432,415 B1 | 8/2002 | Osborne et al. |
| 6,455,066 B1 | 9/2002 | Fischer et al. |
| 6,495,124 B1 | 12/2002 | Samour |
| 6,528,086 B2 * | 3/2003 | Zhang ........................ 424/449 |

(Continued)

FOREIGN PATENT DOCUMENTS

| | | |
|---|---|---|
| CN | 1426815 | 7/2003 |
| CN | 1739487 | 3/2006 |

(Continued)

OTHER PUBLICATIONS

R.D. Wang et al., "Update on ropivacaine" Expert Opin. Pharmacother., 2001, 2(12), pp. 2051-2063.*
Nortier, Y.L.M. et al. "Preparation and stability testing of a hydrogel for topical analgesia," Jul. 1995, pp. 214-217.
An, Na-Mi et al. "Development of a Novel Soft Hydrogel for the Transdermal Delivery of Testosterone," Drug Development and Industrial Pharmacy, 2003, pp. 99-105, vol. 29, No. 1.
Dockrell et al., "Imiquimod and resiquimod as novel immunomodulators" J. Antimicrobial Chemother., 2001, 48, pp. 751-755.

(Continued)

*Primary Examiner* — Brian Gulledge
(74) *Attorney, Agent, or Firm* — Thorpe North & Western LLP

(57) ABSTRACT

The present invention is drawn to adhesive solidifying formulations for treating neuropathic pain. The formulation can include a drug suitable for treating neuropathic pain, a solvent vehicle, and a solidifying agent. The solvent vehicle can include a volatile solvent system including at least one volatile solvent, and a non-volatile solvent system including at least one non-volatile solvent capable of facilitating the delivery of the drug at therapeutically effective rates over a sustained period of time. The formulation can have a viscosity suitable for application to a skin surface prior to evaporation of the volatile solvents system. When applied to the skin, the formulation can form a solidified layer after at least a portion of the volatile solvent system is evaporated.

93 Claims, No Drawings

(56) References Cited

U.S. PATENT DOCUMENTS

| | | | |
|---|---|---|---|
| 6,562,363 B1* | 5/2003 | Mantelle et al. | 424/434 |
| 6,635,674 B1 | 10/2003 | Kaneko et al. | |
| 6,653,346 B1 | 11/2003 | Wang et al. | |
| 6,673,363 B2 | 1/2004 | Luo et al. | |
| 6,962,691 B1 | 11/2005 | Lulla et al. | |
| 7,223,418 B2 | 5/2007 | Hidaka et al. | |
| 2002/0077328 A1 | 6/2002 | Hassan et al. | |
| 2002/0111377 A1 | 8/2002 | Stinchcomb | |
| 2002/0155140 A1 | 10/2002 | Sirinyan et al. | |
| 2003/0018085 A1* | 1/2003 | Raoof et al. | 514/772 |
| 2003/0059471 A1 | 3/2003 | Compton et al. | |
| 2003/0091519 A1 | 5/2003 | Zatz et al. | |
| 2003/0096012 A1 | 5/2003 | Besse et al. | |
| 2003/0118655 A1 | 6/2003 | Kundel | |
| 2003/0185915 A1 | 10/2003 | Carlo et al. | |
| 2004/0018241 A1 | 1/2004 | Houze et al. | |
| 2004/0057985 A1 | 3/2004 | Bracht | |
| 2004/0091534 A1 | 5/2004 | Geoghegan et al. | |
| 2004/0143026 A1 | 7/2004 | Shah | |
| 2005/0089539 A1 | 4/2005 | Scholz et al. | |
| 2005/0158274 A1 | 7/2005 | Hunter et al. | |
| 2005/0276842 A1 | 12/2005 | Zhang et al. | |
| 2007/0189977 A1 | 8/2007 | Zhang et al. | |
| 2007/0189978 A1 | 8/2007 | Zhang et al. | |
| 2007/0189980 A1 | 8/2007 | Zhang et al. | |
| 2007/0190124 A1 | 8/2007 | Zhang et al. | |
| 2007/0196293 A1 | 8/2007 | Zhang et al. | |
| 2007/0196323 A1 | 8/2007 | Zhang et al. | |
| 2007/0196325 A1 | 8/2007 | Zhang et al. | |
| 2007/0196452 A1 | 8/2007 | Zhang et al. | |
| 2007/0196453 A1 | 8/2007 | Zhang et al. | |
| 2007/0196457 A1 | 8/2007 | Zhang et al. | |
| 2007/0196459 A1 | 8/2007 | Zhang et al. | |
| 2007/0280972 A1 | 12/2007 | Zhang et al. | |
| 2008/0019927 A1 | 1/2008 | Zhang et al. | |

FOREIGN PATENT DOCUMENTS

| | | |
|---|---|---|
| EP | 0 002 426 | 6/1979 |
| EP | 0 386 960 | 9/1990 |
| EP | 0 455 396 | 11/1991 |
| GB | 2 004 746 | 4/1979 |
| JP | 01-110620 | 10/1987 |
| JP | 01-110623 | 4/1989 |
| JP | 110620 | 4/1989 |
| JP | 1110623 | 4/1989 |
| JP | 2279623 | 11/1990 |
| JP | 200086440 | 3/2000 |
| JP | 2002226354 | 8/2002 |
| WO | WO 92/13529 | 8/1992 |
| WO | WO 97/29735 | 8/1997 |
| WO | WO 97/38675 | 10/1997 |
| WO | WO 99/22717 | 5/1999 |
| WO | 99/49835 | 10/1999 |
| WO | 0122907 | 4/2001 |
| WO | 0137890 | 5/2001 |
| WO | 01/43722 | 6/2001 |
| WO | 0160325 | 8/2001 |
| WO | WO 02/055023 | 7/2002 |
| WO | WO 03/059390 | 7/2003 |
| WO | WO 03/105821 | 12/2003 |
| WO | 2006097474 | 9/2006 |
| WO | 2007070643 | 6/2007 |
| WO | 2007070679 | 6/2007 |
| WO | 2007070695 | 6/2007 |

OTHER PUBLICATIONS

Khazaeinia et al., "A comparison of gastrointestinal permeability induced by diclofenac phospholipid complex with diclofenac acid and its sodium salt" J. Pharmacy and Pharmaceutical Science; 6(3): 352-359, 2003.

Handbook of Pharmaceutical Excipients (1988) p. 123 (Glycerin) and p. 241 (Propylene Glycol).

Testosterone, Vitamin D May Improve Aromatase Inhibitor Joint Problems; http://www.medconnect.com.sg/tabid/92/ct1/c35097/Testosterone-Vitamin-D-May-Improve-Aromatase-Inhibitor-Joint-Problems/Default.aspx; May 13, 2010; 2 pages.

Panchagnula; "Feasibility studies of dermal delivery of paclitaxel with binary combination of ethanol and isopropyl myristate: roll of solubility, partitioning and lipid bilayer perturbation"; Farmaco, vol. 60, No. 11-12, Aug. 26, 2005 pp. 894-899.

Kondo; "Enhancement of transdermal delivery by superfluous thermodynamic potential. I. Thermodynamic analysis of nifedipine transport across the lipoidal barrier"; J. Pharmacobiodyn, vol. 10, Apr. 17, 1987, pp. 587-594.

Loceryl; "Scary Nails?"; http://www.loceryl.com.au; the Australian associate on Apr. 19, 2013.

Mackowiak; Clinical Infectious Diseases (2000) vol. 31 (Suppl. 5): p. S154-6.

Anonymous, Dermatological and Transdermal Formulations, Chapter 6, 2002 by Marcel Dekker, Inc., pp. 282-284, (case annex, Chapter 6, Formulation Strategies for Modulating Skin Permeation, Davis et al.).

Padilla et al., Topical Medications for Orofacial Neuropathic Pain: A Review, JADA, vol. 131, Feb. 2000, pp. 184-195.

Farber et al., Serotonergic Agents That Activate 5HT2A Receptors Prevent NMDA Antagonist Neurotoxicity, Neuropsychopharmacology, vol. 18, No. 1, 1998, pp. 57-62.

CAMEO Chemicals, Chemical data sheet for Difluoroethane (2 pages) obtained from http://cameochemicals.noaa.gov/chemical/565, 2014.

* cited by examiner

COMPOSITIONS AND METHODS FOR DERMALLY TREATING NEUROPATHIC PAIN

This application claims the benefit of U.S. Provisional Application Nos. 60/750,637 and 60/750,519, each of which was filed on Dec. 14, 2005, and is a continuation-in-part of U.S. application Ser. No. 11/146,917 filed on Jun. 6, 2005, which claims the benefit of U.S. Provisional Application No. 60/577,536 filed on Jun. 7, 2004, each of which is incorporated herein by reference.

FIELD OF THE INVENTION

The present invention relates generally to formulations and methods developed for treating neuropathic pain. More particularly, the present invention relates to adhesive solidifying formulations having a viscosity suitable for application to a skin surface, and which form a sustained drug-delivering adhesive solidified layer on the skin.

BACKGROUND OF THE INVENTION

Neuropathic pain can be caused by various underlying diseases, such as viral infections and diabetes. For example, post herpetic neuralgia is caused by herpes viral infection and typically causes moderate to severe pain in the infected skin area to the subject. Topical products, such as creams or patches containing appropriate drugs, may be used to control neuropathic pain; however, patches and traditional semisolid formulations such as creams and ointments both have significant shortcomings. Semisolid formulations usually contain solvent(s), such as water and ethanol, which are volatile and thus evaporate shortly after application. The evaporation of such solvents can cause significant decrease or even termination of dermal drug delivery, which can be undesirable in many cases. Additionally, semisolid formulations are often "rubbed into" the skin, which does not necessarily mean the drug formulation is actually delivered into the skin. Instead, this phrase often means that a very thin layer of the drug formulation is applied onto the surface of the skin. Such thin layers of traditional semisolid formulations applied to the skin may not contain sufficient quantity of the active drug to achieve sustained delivery over long periods of time, which can be desirable in treating neuropathic pain. Additionally, traditional semisolid formulations are often subject to unintentional removal due to contact with objects such as clothing, which may compromise the sustained delivery and/or undesirably soil clothing.

A patch containing an appropriate drug can be used to treat neuropathic pain. However, subjects often have to cut the patch to fit the shape and size of the skin area to be treated, which is inconvenient. Another shortcoming of patches is that they are usually neither sufficiently stretchable nor flexible for every application location because the backing film (in matrix patches) and the thin fluid bag (in reservoir patches) are typically made of polyethylene or polyester, both of which are relatively non-stretchable materials. If the patch is applied on a skin area that is significantly stretched during body movements, such as joints and muscles, separation between the patch and skin may occur, thereby compromising the delivery of the drug. In addition, a patch on a skin surface may hinder the expansion of the skin during body movements and cause discomfort and/or aggravate pain. For these additional reasons, patches are not ideal dosage forms for skin areas subject to expansion and stretching during body movements.

In view of these and other shortcomings, it would be desirable to provide systems, formulations, and/or methods for treating neuropathic pain that i) can provide sustained drug delivery over long periods of time; ii) are not vulnerable to unintentional removal by contact with either clothing, other objects, or with other people for the duration of the application time; iii) can be applied to a skin area subject to stretching and expansion without causing discomfort or poor contact to skin; and/or iv) can be easily removed after application and use.

SUMMARY OF THE INVENTION

It has been recognized that it would be advantageous to provide topical neuropathic pain treatment formulations, systems, and/or methods in the form of adhesive solidifying compositions or formulations having a viscosity suitable for application to a skin surface as a layer, and which form a drug-delivering solidified layer on the skin that is easily peelable or removable after use.

In accordance with this, a formulation for treating neuropathic pain can comprise a drug suitable for treating neuropathic pain, a solvent vehicle, and a solidifying agent. The solvent vehicle can include a volatile solvent system comprising at least one volatile solvent, and a non-volatile solvent system comprising at least one non-volatile solvent. The non-volatile solvent system facilitates dermal delivery of the drug at a therapeutically effective rate over a sustained period of time. The formulation can have a viscosity suitable for application and adhesion to a skin surface as a layer prior to evaporation of the volatile solvent system. The formulation applied to the skin surface can form a solidified layer after at least partial evaporation of the volatile solvent system. Further, the drug can continue to be delivered at the therapeutically effective rate after the volatile solvent system is at least substantially evaporated.

In another embodiment, a method for treating neuropathic pain can comprise the step of applying a layer of an adhesive formulation to a skin surface of a subject. The formulation can comprise a drug suitable for treating neuropathic pain, a solvent vehicle, and a solidifying agent. The solvent vehicle can comprise a volatile solvent system including at least one volatile solvent, and a non-volatile solvent system including at least one non-volatile solvent. The non-volatile solvent system facilitates dermal delivery of the drug at a therapeutically effective rate over a sustained period of time. The formulation can have a viscosity suitable for application and adhesion to a skin surface prior to evaporation of the volatile solvent system. Additional steps include solidifying the formulation to form a solidified layer on the skin surface by at least partial evaporation of the volatile solvent system; and dermally delivering the drug from the solidified layer to the subject at therapeutically effective rates over a sustained period of time to reduce the neuropathic pain.

In another embodiment, a solidified layer for treating neuropathic pain can comprise a drug suitable for treating neuropathic pain, a non-volatile solvent system suitable for the drug, and a solidifying agent. The solidified layer can have sufficient elasticity, flexibility, and adhesion to the skin so that it is not separated from the skin even if the skin surface is stretched or bent during a subject's normal daily activities. For example, the solidified layer can be stretchable by 5% in one direction without cracking, breaking, and/or separating from a skin surface to which the layer is applied.

In another embodiment, a formulation for treating neuropathic pain can comprise ropivacaine, a solvent vehicle, and a solidifying agent. The solvent vehicle can comprise a volatile solvent system including at least one volatile solvent, and a non-volatile solvent system can include at least one solvent selected from the group consisting of an amine base, triacetin, span 20, isostearic acid, or a mixture thereof. The solidifying agent can include butyl and methyl methacrylate copolymers. The formulation can have a viscosity suitable for application to a skin surface as a layer prior to evaporation of the volatile solvent system. Further, formulation layer applied to the skin surface can form a solidified, coherent, flexible, and continuous layer after at least partial evaporation of the volatile solvent system. The ropivacaine can also continue to be delivered at a therapeutically effective rate after the volatile solvent system is at least substantially all evaporated.

In another embodiment, a formulation for treating neuropathic pain associated with viral infections can comprise a drug, a solvent vehicle, and a solidifying agent. The drug can include a member selected from the group consisting of acyclovir, valacyclovir, and pencyclovir. The solvent vehicle can include a volatile solvent system including at least one volatile solvent, and a non-volatile solvent system comprising at least one solvent selected from the group of oleic acid, isostearic acid, and olive oil. The solidifying agent can be selected from the group consisting of ethyl acrylate-methyl methacrylate-trimethylammonioethyl methacrylate chloride copolymers, butyl and methyl methacrylae copolymers, and ethyl cellulose. The formulation can have a viscosity suitable for application to a skin surface as a layer prior to evaporation of the volatile solvent system. Further, formulation applied to the skin surface can form a solidified, coherent, flexible, and continuous layer after at least partial evaporation of the volatile solvent system. The drug can also continue to be delivered at a therapeutically effective rate after the volatile solvent system is at least substantially all evaporated.

In another embodiment, a formulation for treating neuropathic pain can comprise a local anesthetic selected from the group consisting of lidocaine, tetracaine, and a combination thereof; a solvent vehicle; and a solidifying agent. The solvent vehicle can comprise a volatile solvent system including at least one volatile solvent, and a non-volatile solvent system including at least one solvent selected from the group consisting of propylene glycol and dipropylene glycol. The local anesthetic can be in either base or salt form, and the formulation can have a viscosity suitable for application to a skin surface prior to evaporation of the volatile solvent system. The formulation applied to the skin surface can form a solidified, coherent, flexible and continuous layer after at least partial evaporation of the volatile solvent system, and the local anesthetic can continue to be delivered at a therapeutically effective rate after the volatile solvent system is at least substantially all evaporated.

In another embodiment, a formulation for treating neuropathic pain can comprise a drug selected from the group consisting of amitriptyline, ketamine, and combinations thereof; a solvent vehicle; and a solidifying agent. The solvent vehicle can comprise a volatile solvent system including at least one volatile solvent, and a non-volatile solvent system comprising at least one non-volatile solvent. The formulation can have a viscosity suitable for application to a skin surface prior to evaporation of the volatile solvent system. The formulation applied to the skin surface can form a solidified, coherent, flexible and continuous layer after at least partial evaporation of the volatile solvent system. Further, the drug can continue to be delivered at a therapeutically effective rate after the volatile solvent system is at least substantially all evaporated.

In another embodiment, a formulation for treating neuropathic pain can comprise a drug selected from the group consisting of lidocaine, tetracaine, ropivacaine, amitriptyline, ketamine, and combinations thereof; a solvent vehicle; and a solidifying agent. The solvent vehicle can include a volatile solvent system comprising a volatile solvent whose boiling point is below 20° C., and a non-volatile solvent system comprising at least one non-volatile solvent. The formulation can have a viscosity suitable for application to a skin surface prior to evaporation of the volatile solvent system, and when applied to the skin surface, can form a solidified, coherent, flexible and continuous layer after at least partial evaporation of the volatile solvent system. The drug can continue to be delivered at a therapeutically effective rate after the volatile solvent system is at least substantially all evaporated.

Additional features and advantages of the invention will be apparent from the following detailed description which illustrates, by way of example, features of the invention.

DETAILED DESCRIPTION OF THE PREFERRED EMBODIMENT(S)

Before particular embodiments of the present invention are disclosed and described, it is to be understood that this invention is not limited to the particular process and materials disclosed herein as such may vary to some degree. It is also to be understood that the terminology used herein is used for the purpose of describing particular embodiments only and is not intended to be limiting, as the scope of the present invention will be defined only by the appended claims and equivalents thereof.

In describing and claiming the present invention, the following terminology will be used.

The singular forms "a," "an," and "the" include plural referents unless the context clearly dictates otherwise. Thus, for example, reference to "a drug" includes reference to one or more of such compositions.

"Skin" is defined to include human skin (intact, diseased, ulcerous, or broken), finger and toe nail surfaces, and mucosal surfaces that are usually at least partially exposed to air such as lips, genital and anal mucosa, and nasal and oral mucosa.

The term "drug(s)" or "drug(s) suitable for treating neuropathic pain" refers to any bioactive agent that is applied to, into, or through the skin for preventing and/or treating neuropathic pain and/or underlying diseases or causes of diseases. One example of neuropathic pain associated with herpes is shingles, which can be treated in accordance with embodiments of the present invention. Other examples of sources of neuropathic pain include pain associate with diabetes, pain associated with postherpatic neuralgia, and pain associated with postsurgical/post-traumatic conditions. Examples of drugs suitable for treating neuropathic pain include, without limitation, local anesthetics including lidocaine, bupivacaine, ropivacaine, and tetracaine; steroids including dexamethasone; alpha-2 agonists including clonidine; tricyclic anti-depressants including amitriptyline, anti-convulsants, N-methyl-D-aspartate (NMDA) antagonists including dextromethorphan, memantine, amantadine, ketamine, methadone, dextropropoxyphene, and ketobemidone; antiviral drugs including acyclovir, penciclovir, famciclovir, valacyclovir steroids; 5-HT2A receptor antagonist including ketanserin; or combinations thereof.

The phrases "dermal drug delivery" or "dermal delivery of drug(s)" shall include both transdermal and topical drug delivery, and includes the delivery of drug(s) to, through, or into the skin. "Transdermal delivery" of drug can be targeted to skin tissues just under the skin, regional tissues or organs under the skin, systemic circulation, and/or the central nervous system.

The term "flux" such as in the context of "dermal flux" or "transdermal flux," respectively, refers to the quantity of the drug permeated into or across skin per unit area per unit time. A typical unit of flux is microgram per square centimeter per hour. One way to measure flux is to place the formulation on a known skin area of a human volunteer and measure how much drug can permeate into or across skin within certain time constraints. Various methods (in vivo methods) might be used for the measurements as well. The method described in Example 1 or other similar method (in vitro methods) can also be used to measure flux. Although an in vitro method uses human epidermal membrane obtained from a cadaver, or freshly separated skin tissue from hairless mice rather than measure drug flux across the skin using human volunteers, it is generally accepted by those skilled in the art that results from a properly designed and executed in vitro test can be used to estimate or predict the results of an in vivo test with reasonable reliability. Therefore, "flux" values referenced in this patent application can mean that measured by either in vivo or in vitro methods.

The term "flux-enabling" with respect to the non-volatile solvent system (or solidified layer including the same) refers to a non-volatile solvent system (including one or more non-volatile solvents) selected or formulated specifically to be able to provide therapeutically effective flux for a particular drug(s). For topically or regionally delivered drugs, a flux enabling non-volatile solvent system is defined as a non-volatile solvent system which, alone without the help of any other ingredients, is capable of delivering therapeutic effective levels of the drug across, onto or into the subject's skin when the non-volatile solvent system is saturated with the drug. For systemically targeted drugs, a flux enabling non-volatile solvent system is a non-volatile solvent system that can provide therapetucially sufficient daily doses over 24 hours when the non-volatile solvent system is saturated with the drug and is in full contact with the subject's skin with no more than 500 $cm^2$ contact area. Preferably, the contact area for the non-volatile solvent system is no more than 100 $cm^2$. Testing using this saturated drug-in-solvent state can be used to measure the maximum flux-generating ability of a non-volatile solvent system. To determine flux, the drug solvent mixture needs to be kept on the skin for a clinically sufficient amount of time. In reality, it may be difficult to keep a liquid solvent on the skin of a human volunteer for an extended period of time. Therefore, an alternative method to determine whether a solvent system is "flux-enabling" is to measure the in vitro drug permeation across the hairless mouse skin or human cadaver skin using the apparatus and method described in Example 1. This and similar methods are commonly used by those skilled in the art to evaluate permeability and feasibility of formulations. Alternatively, whether a non-volatile solvent system is flux-enabling can be tested on the skin of a live human subject with means to maintain the non-volatile solvent system with saturated drug on the skin, and such means may not be practical for a product. For example, the non-volatile solvent system with saturated drug can be soaked into an absorbent fabric material which is then applied on the skin and covered with a protective membrane. Such a system is not practical as a pharmaceutical product, but is appropriate for testing whether a non-volatile solvent system has the intrinsic ability to provide sufficient drug flux, or whether it is flux-enabling.

It is also noted that once the formulation forms a solidified layer, the solidified layer can also be "flux enabling" for the drug while some of the non-volatile solvents remain in the solidified layer, even after the volatile solvents (including water) have been substantially evaporated.

For lidocaine base, a non-volatile solvent system would be "flux enabling" if it is capable of generating a flux of at least about 20 $mcg/cm^2/hour$ in a setup same or similar to that described in Example 1. For tetracaine and ropivacaine bases, a non-volatile solvent system would be "flux enabling" if it is capable of generating a flux of at least about 5 $mcg/cm^2/hour$ in a setup same or similar to that described in Example 1. For amitriptyline, a non-volatile solvent system would be "flux enabling" if it is capable of generating a flux of about at least 5 $mcg/cm^2/hour$ in a setup same or similar to that described in Example 1. For an alpha-2 agonist or ketamine, the non-volatile solvent system would be "flux enabling" if it is capable of generating a flux of at least about 1 $mcg/cm^2/hour$ in a setup same or similar to that described in Example 1. For capsaicin, the non-volatile solvent system would be "flux enabling" if it is capable of generating a flux of at least about 5 $mcg/cm^2/hour$ in a setup same or similar to that described in Example 1.

For example, the importance of selecting an appropriate non-volatile solvent is demonstrated in Table 1. The flux of ropivacaine (a local anesthetic agent effective in treating neuropathic pain) from saturated glycerol, isostearic acid (ISA) alone and ISA+trolamine, and ISA+trolamine peel are presented in Table 1. Flux values were generated in an in vitro experiment described below in Example 1. The estimated therapeutically beneficial ropicavaine flux is 5-10 $mcg/cm^2/h$.

TABLE 1

| Non-volatile solvent | In vitro flux ($mcg/cm^2/h$)* |
|---|---|
| ISA | 11 ± 2 |
| ISA + 20% trolamine | 43 ± 7 |
| ISA + trolamine peel | 32 ± 2 |
| Glycerol | 1.2 ± 0.7 |

Estimated therapeutically beneficial flux = 5-10 $mcg/cm^2/h$
*In vitro flux values represent the mean and st. dev. of three determinations.

In vitro flux results of ropivacaine from ISA, and ISA+trolamine are examples of a suitable non-volatile solvent, and glycerol is an example of an unsuitable non-volatile solvent. When incorporated into a solidifying formulation, the suitable non-volatile solvent dictates the flux-generating power of the formulation. It should be noted that a non-volatile solvent system suitable for the selected drug can be a single chemical substance or a mixture of two or more chemical substances. As can be seen above, the non-volatile solvent system of ISA+trolamine can generate more flux than the non-volatile solvent system of pure ISA, though both are probably suitable for certain applications.

The phrase "effective amount," "therapeutically effective amount,""therapeutically effective rate(s)," or the like, as it relates to a drug, refers to sufficient amounts or delivery rates of a drug which achieves any appreciable level of therapeutic results in treating a condition for which the drug is being delivered. It is understood that "appreciable level of therapeutic results" may or may not meet any government agencies' efficacy standards for approving the commercialization of a product. It is understood that various biological factors may affect the ability of a substance to perform its intended task. Therefore, an "effective amount," "therapeutically effective amount," or "therapeutically effective rate(s)" may be dependent in some instances on such biological factors to some degree. However, for each drug, there is usually a consensus among those skilled in the art on the range of doses or fluxes that are sufficient in most subjects. Further, while the achievement of therapeutic effects may be measured by a physician or other qualified medical personnel using evaluations known in the art, it is recognized that individual variation and response to treatments may make the achievement of therapeutic effects a subjective decision. The determination of a therapeutically effective amount or delivery rate is well within the ordinary skill in the art of pharmaceutical sciences and medicine.

"Therapeutically effective flux" refers to the permeation flux of the selected drug that delivers sufficient amount of drug into or across the skin to be clinically beneficial in that some of the patient population can obtain some degree of benefit from the drug flux. It does not necessarily mean that most of the patient population can obtain some degree of benefit or the benefit is high enough to be deemed "effective" by relevant government agencies or the medical profession. More specifically, for drugs that target skin or regional tissues or organs close to the skin surface (such as joints, certain muscles, or tissues/organs that are at least partially within 5 cm of the skin surface), "therapeutically effective flux" refers to the drug flux that can deliver a sufficient amount of the drug into the target tissues within a clinically reasonable amount of time. For drugs that target the systemic circulation, "therapeutically effective flux" refers to drug flux that, via clinically reasonable skin contact area, can deliver sufficient amounts of the selected drug to generate clinically beneficial plasma or blood drug concentrations within a clinically reasonable time. Clinically reasonable skin contact area is defined as a size of skin application area that most subjects would accept. Typically, a skin contact area of 400 $cm^2$ or less is considered reasonable. Therefore, in order to deliver 4000 mcg of a drug to the systemic circulation via a 400 $cm^2$ skin contact area over 10 hours, the flux needs to be at least 4000 mcg/400 $cm^2$/10 hour, which equals 1 $mcg/cm^2/hr$. By this definition, different drugs have different "therapeutically effective flux." Thus, a therapeutically effective flux may be different in different subjects and or at different times for even the same subject. However, for each drug, there is usually a consensus among the skilled in the art on the range of doses or fluxes that are sufficient in most subjects for a given drug or treatment.

It should be noted that "flux-enabling non-volatile solvent," "flux-enabling, plasticizing non-volatile solvent," or "high flux-enabling non-volatile solvent" can be a single chemical substance or a mixture of two or more chemical substances. For example, the steady state flux value for clobetasol propionate in Table C is a 9:1 for propylene glycol:isostearic acid mixture that generated much higher clobetasol flux than propylene glycol or ISA alone (see Table B). Therefore, the 9:1 propylene glycol:isostearic acid mixture is a "high flux-enabling non-volatile solvent" but propylene glycol or isostearic acid alone is not.

The term "adhesion" or "adhesive" when referring to a solidified layer herein refers to sufficient adhesion between the solidified layer and the skin so that the layer does not fall off the skin during intended use on most subjects. Thus, "adhesive" or the like when used to describe the solidified layer means the solidified layer is adhesive to the body surface to which the initial formulation layer was originally applied (before the evaporation of the volatile solvent(s)). In one embodiment, it does not mean the solidified layer is adhesive on the opposing side. In addition, it should be noted that whether a solidified layer can adhere to a skin surface for the desired extended period of time partially depends on the condition of the body surface. For example, excessively sweating or oily skin, or oily substances on the skin surface may make the solidified layer less adhesive to the skin. Therefore, the adhesive solidified layer of the current invention may not be able to maintain perfect contact with the body surface and deliver the drug over a sustained period of time for every subject under any conditions on the body surface. A standard is that it maintains good contact with most of the body surface, e.g. 70% of the total area, over the specified period of time for most subjects under normal conditions of the body surface and external environment.

The terms "flexible," "elastic," "elasticity," or the like, as used herein refer to sufficient elasticity of the solidified layer so that it is not broken if it is stretched in at least one direction by up to about 5%, and often to about 10% or even greater. For example, a solidified layer that exhibits acceptably elasticity and adhesion to skin can be attached to human skin over a flexible skin location, e.g., elbow, finger, wrist, neck, lower back, lips, knee, etc., and will remain substantially intact on the skin upon stretching of the skin. It should be noted that the solidified layers of the present invention do not necessarily have to have any elasticity in some embodiments.

The term "peelable," when used to describe the solidified layer, means the solidified layer can be lifted from the skin surface in one large piece or several large pieces, as opposed to many small pieces or crumbs.

The term "sustained" relates to therapeutically effective rates of dermal drug delivery for a continuous period of time of at least 30 minutes, and in some embodiments, periods of time of at least about 2 hours, 4 hours, 8 hours, 12 hours, 24 hours, or longer.

The use of the term "substantially" when referring to the evaporation of the volatile solvents means that a majority of the volatile solvents which were included in the initial formulation have evaporated. Similarly, when a solidified layer is said to be "substantially devoid" of volatile solvents, including water, the solidified layer has less than 10 wt %, and preferably less than 5 wt %, of the volatile solvents in the solidified layer as a whole.

"Volatile solvent system" can be a single solvent or a mixture of solvents that are volatile, including water and solvents that are more volatile than water. Non-limiting examples of volatile solvents that can be used in the present invention include denatured alcohol, methanol, ethanol, isopropyl alcohol, water, propanol, C4-C6 hydrocarbons, butane, isobutene, pentane, hexane, acetone, ethyl acetate, fluro-chloro-hydrocarbons, methyl ethyl ketone, methyl ether, hydrofluorocarbons, ethyl ether, 1,1,1,2 tetrafluorethane 1,1,1,2,3,3,3-heptafluoropropane, 1,1,1,3,3,3 hexafluoropropane, or combinations thereof.

"Non-volatile solvent system" can be a single solvent or mixture of solvents that are less volatile than water. It can also contain substances that are solid or liquid at room temperatures, such as pH or ion-pairing agents. After evaporation of the volatile solvent system, most of the non-volatile solvent system should remain in the solidified layer for an amount of time sufficient to dermally delivery a given drug to, into, or through the skin of a subject at a sufficient flux for a period of time to provide a therapeutic effect. In some embodiments, in order to obtain desired permeability for an active drug and/or compatibility with solidifying agents or other ingredients of the formulation, a mixture of two or more non-volatile solvents can be used to form the non-volatile solvent system. In one embodiment, the combination of two or more non-volatile solvents to form a solvent system provides a higher transdermal flux for a drug than the flux provided for the drug by each of the non-volatile solvents individually. The non-volatile solvent system may also serve as a plasticizer of the solidified layer, so that the solidified layer is elastic and flexible.

The term "solvent vehicle" describes compositions that include both a volatile solvent system and non-volatile solvent system. The volatile solvent system is chosen so as to evaporate from the adhesive peelable formulation quickly to form a solidified layer, and the non-volatile solvent system is formulated or chosen to substantially remain as part of the solidified layer after volatile solvent system evaporation so as to provide continued delivery of the drug. Typically, the drug can be partially or completely dissolved in the solvent vehicle or formulation as a whole. Likewise, the drug can also be partially or completely solubilizable in the non-volatile solvent system once the volatile solvent system is evaporated. Formulations in which the drug is only partially dissolved in the non-volatile solvent system after the evaporation of the volatile solvent system have the potential to maintain longer duration of sustained delivery, as the undissolved drug can dissolve into the non-volatile solvent system as the dissolved drug is being depleted from the solidified layer during drug delivery.

"Adhesive solidifying formulation" or "solidifying formulation" refers to a composition that has a viscosity suitable for application to a skin surface prior to evaporation of its volatile solvent(s), and which can become a solidified layer after evaporation of at least a portion of the volatile solvent(s). The solidified layer, once formed, can be very durable. In one embodiment, once solidified on a skin surface, the formulation can form a peel. The peel can be a soft, coherent solid that can be removed by peeling large pieces from the skin relative to the size of the applied formulation, and often, can be peeled from the skin as a single piece. The application viscosity is typically more viscous than a water-like liquid, but less viscous than a soft solid. Examples of preferred viscosities include materials that have consistencies similar to pastes, gels, ointments, and the like, e.g., viscous liquids that flow but are not subject to spilling. Thus, when a composition is said to have a viscosity "suitable for application" to a skin surface, this means the composition has a viscosity that is high enough so that the composition does not substantially run off the skin after being applied to skin, but also has a low enough viscosity so that it can be easily spread onto the skin. A viscosity range that meets this definition can be from about 100 cP to about 3,000,000 cP (centipoises), and more preferably from about 1,000 cP to about 1,000,000 cP.

In some embodiments of the present invention it may be desirable to add an additional agent or substance to the formulation so as to provide enhanced or increased adhesive characteristics. The additional adhesive agent or substance can be an additional non-volatile solvent or an additional solidifying agent. Non-limiting examples of substances which might be used as additional adhesion enhancing agents include copolymers of methylvinyl ether and maleic anhydride (Gantrez polymers), polyethylene glycol and polyvinyl pyrrolidone, gelatin, low molecular weight polyisobutylene rubber, copolymer of acrylsan alkyl/octylacrylamido (Dermacryl 79), and various aliphatic resins and aromatic resins.

The terms "washable," "washing," or "removed by washing" when used with respect to the adhesive formulations of the present invention refers to the ability of the adhesive formulation to be removed by the application of a washing solvent using a normal or medium amount of washing force. The required force to remove the formulations by washing should not cause significant skin irritation or abrasion. Generally, gentle washing force accompanied by the application of an appropriate washing solvent is sufficient to remove the adhesive formulations disclosed herein. The solvents which can be used for removing by washing the formulations of the present invention are numerous, but preferably are chosen from commonly acceptable solvents including the volatile solvents listed herein. Preferred washing solvents do not significantly irritate human skin and are generally available to the average subject. Examples of washing solvents include but are not limited to water, ethanol, methanol, isopropyl alcohol, acetone, ethyl acetate, propanol, or combinations thereof. In aspect of the invention the washing solvents can be selected from the group consisting of water, ethanol, isopropyl alcohol or combinations thereof. Surfactants can also be used in some embodiments.

Acceptable lengths of time when referring to "drying time" refers to the time it takes for the formulation to form a non-messy solidified surface after application on skin under standard skin and ambient conditions, and with standard testing procedure. It is noted that the word "drying time" in this application does not mean the time it takes to completely evaporate off the volatile solvent(s). Instead, it means the time it takes to form the non-messy solidified surface as described above.

"Standard skin" is defined as dry, healthy human skin with a surface temperature of between about 30° C. to about 36° C. Standard ambient conditions are defined by the temperature range of from 20° C. to 25° C. and a relative humidity range of from 20% to 80%. The term "standard skin" in no way limits the types of skin or skin conditions on which the formulations of the present invention can be used. The formulations of the present invention can be used to treat all types of "skin," including undamaged (standard skin), diseased skin, or damaged skin. Although skin conditions having different characteristics can be treated using the formulations of the present invention, the use of the term "standard skin" is used merely as a standard to test the compositions of the varying embodiments of the present invention. As a practical matter, formulations that perform well (e.g., solidify, provide therapeutically effective flux, etc.) on standard skin can also perform well diseased or damaged skin.

The "standard testing procedure" or "standard testing condition" is as follows: To standard skin at standard ambient conditions is applied an approximately 0.1 mm layer of the adhesive solidifying formulation and the drying time is measured. The drying time is defined as the time it takes for the formulation to form a non-messy surface such that the formulation does not lose mass by adhesion to a piece of 100% cotton cloth pressed onto the formulation surface with a pressure of between about 5 and about 10 g/cm$^2$ for 5 seconds.

"Solidified layer" describes the solidified or dried layer of an adhesive solidifying formulation after at least a portion of the volatile solvent system has evaporated. The solidified layer remains adhered to the skin, and is preferably capable of maintaining good contact with the subject's skin for substantially the entire duration of application under standard skin and ambient conditions. The solidified layer also preferably exhibits sufficient tensile strength so that it can be peeled off the skin at the end of the application in one piece or several large pieces (as opposed to a layer with weak tensile strength that breaks into many small pieces or crumbles when removed from the skin).

As used herein, a plurality of drugs, compounds, and/or solvents may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.01 to 2.0 mm" should be interpreted to include not only the explicitly recited values of about 0.01 mm to about 2.0 mm, but also include individual values and sub-ranges within the indicated range. Thus, included in this numerical range are individual values such as 0.5, 0.7, and 1.5, and sub-ranges such as from 0.5 to 1.7, 0.7 to 1.5, and from 1.0 to 1.5, etc. This same principle applies to ranges reciting only one numerical value. Furthermore, such an interpretation should apply regardless of the breadth of the range or the characteristics being described.

With these definitions in mind, a formulation for treating neuropathic pain can comprise a drug suitable for treating neuropathic pain, a solvent vehicle, and a solidifying agent. The solvent vehicle can include a volatile solvent system comprising at least one volatile solvent, and a non-volatile solvent system comprising at least one non-volatile solvent. The non-volatile solvent system facilitates dermal delivery of the drug at a therapeutically effective rate over a sustained period of time. The formulation can have a viscosity suitable for application and adhesion to a skin surface as a layer prior to evaporation of the volatile solvent system. The formulation applied to the skin surface can form a solidified layer after at least partial evaporation of the volatile solvent system. Further, the drug can continue to be delivered at the therapeutically effective rate after the volatile solvent system is at least substantially evaporated.

In another embodiment, a method for treating neuropathic pain can comprise the step of applying a layer of an adhesive formulation to a skin surface of a subject. The formulation can comprise a drug suitable for treating neuropathic pain, a solvent vehicle, and a solidifying agent. The solvent vehicle can comprise a volatile solvent system including at least one volatile solvent, and a non-volatile solvent system including at least one non-volatile solvent. The non-volatile solvent system facilitates dermal delivery of the drug at a therapeutically effective rate over a sustained period of time. The formulation can have a viscosity suitable for application and adhesion to a skin surface prior to evaporation of the volatile solvent system. Additional steps include solidifying the formulation to form a solidified layer on the skin surface by at least partial evaporation of the volatile solvent system; and dermally delivering the drug from the solidified layer to the subject at therapeutically effective rates over a sustained period of time to reduce the neuropathic pain.

In another embodiment, a solidified layer for treating neuropathic pain can comprise a drug suitable for treating neuropathic pain, a non-volatile solvent system suitable for the drug, and a solidifying agent. The solidified layer can have sufficient elasticity, flexibility, and adhesion to the skin so that it is not separated from the skin even if the skin surface is stretched or bent during a subject's normal daily activities. For example, the solidified layer can be stretchable by 5% in one direction without cracking, breaking, and/or separating from a skin surface to which the layer is applied.

In another embodiment, a formulation for treating neuropathic pain can comprise ropivacaine, a solvent vehicle, and a solidifying agent. The solvent vehicle can comprise a volatile solvent system including at least one volatile solvent, and a non-volatile solvent system can include at least one solvent selected from the group consisting of an amine base, triacetin, span 20, isostearic acid, or a mixture thereof. The solidifying agent can include butyl and methyl methacrylate copolymers. The formulation can have a viscosity suitable for application to a skin surface as a layer prior to evaporation of the volatile solvent system. Further, formulation layer applied to the skin surface can form a solidified, coherent, flexible, and continuous layer after at least partial evaporation of the volatile solvent system. The ropivacaine can also continue to be delivered at a therapeutically effective rate after the volatile solvent system is at least substantially all evaporated.

In another embodiment, a formulation for treating neuropathic pain associated with viral infections can comprise a drug, a solvent vehicle, and a solidifying agent. The drug can include a member selected from the group consisting of acyclovir, valacyclovir, and pencyclovir. The solvent vehicle can include a volatile solvent system including at least one volatile solvent, and a non-volatile solvent system comprising at least one solvent selected from the group of oleic acid, isostearic acid, and olive oil. The solidifying agent can be selected from the group consisting of ethyl acrylate-methyl methacrylate-trimethylammonioethyl methacrylate chloride copolymers, butyl and methyl methacrylae copolymers, and ethyl cellulose. The formulation can have a viscosity suitable for application to a skin surface as a layer prior to evaporation of the volatile solvent system. Further, formulation applied to the skin surface can form a solidified, coherent, flexible, and continuous layer after at least partial evaporation of the volatile solvent system. The drug can also continue to be delivered at a therapeutically effective rate after the volatile solvent system is at least substantially all evaporated.

In another embodiment, a formulation for treating neuropathic pain can comprise a local anesthetic selected from the group consisting of lidocaine, tetracaine, and a combination thereof; a solvent vehicle; and a solidifying agent. The solvent vehicle can comprise a volatile solvent system including at least one volatile solvent, and a non-volatile solvent system including at least one solvent selected from the group consisting of propylene glycol and dipropylene glycol. The local anesthetic can be in either base or salt form, and the formulation can have a viscosity suitable for application to a skin surface prior to evaporation of the volatile solvent system. The formulation applied to the skin surface can form a solidified, coherent, flexible and continuous layer after at least partial evaporation of the volatile solvent system, and the local anesthetic can continue to be delivered at a therapeutically effective rate after the volatile solvent system is at least substantially all evaporated.

In another embodiment, a formulation for treating neuropathic pain can comprise a drug selected from the group consisting of amitriptyline, ketamine, and combinations thereof; a solvent vehicle; and a solidifying agent. The solvent vehicle can comprise a volatile solvent system including at least one volatile solvent, and a non-volatile solvent system comprising at least one non-volatile solvent. The formulation can have a viscosity suitable for application to a skin surface prior to evaporation of the volatile solvent system. The formulation applied to the skin surface can form a solidified, coherent, flexible and continuous layer after at least partial evaporation of the volatile solvent system. Further, the drug can continue to be delivered at a therapeutically effective rate after the volatile solvent system is at least substantially all evaporated.

In another embodiment, a formulation for treating neuropathic pain can comprise a drug selected from the group consisting of lidocaine, tetracaine, ropivacaine, amitriptyline, ketamine, and combinations thereof; a solvent vehicle; and a solidifying agent. The solvent vehicle can include a volatile solvent system comprising a volatile solvent whose boiling point is below 20° C., and a non-volatile solvent system comprising at least one non-volatile solvent. The formulation can have a viscosity suitable for application to a skin surface prior to evaporation of the volatile solvent system, and when applied to the skin surface, can form a solidified, coherent, flexible and continuous layer after at least partial evaporation of the volatile solvent system. The drug can continue to be delivered at a therapeutically effective rate after the volatile solvent system is at least substantially all evaporated.

Thus, the present invention is related to novel formulations, methods, and solidified layers that are typically related to initial formulations of semi-solids (including creams, gels, pastes, ointments, and other viscous liquids), which can be easily applied onto the skin as a layer, and can quickly (from 15 seconds to 4 minutes under standard skin and ambient conditions) to moderately quickly (from 4 to 15 minutes under standard skin and ambient conditions) change into a solidified layer, e.g., a coherent and soft solid layer, for drug delivery for reducing neuropathic pain. A solidified layer thus formed is capable of delivering drug to the skin, into the skin, across the skin, etc., at therapeutically effective rates, over a sustained period of time, e.g., hours to tens of hours, so that most of the drug delivery occurs after the solidified layer is formed. Additionally, the solidified layer typically adheres to the skin, but has a solidified, minimally-adhering, outer surface which is formed relatively soon after application and which does not substantially transfer to or otherwise soil clothing or other objects that a subject is wearing or that the solidified layer may inadvertently contact. The solidified layer can preferably also be formulated such that it is highly flexible and stretchable, and thus capable of maintaining good contact with a skin surface, even if the skin is stretched during body movement, such as at a knee, finger, elbow, or other joints.

In selecting the various components that can be used, e.g., drug, solvent vehicle of volatile solvent system and non-volatile solvent system, solidifying agent(s), etc., various considerations can occur. For example, the volatile solvent system can be selected from pharmaceutically or cosmetically acceptable solvents known in the art. In one embodiment of the present invention the volatile solvent system can include ethanol, isopropyl alcohol, water, dimethyl ether, diethyl ether, butane, propane, isobutene, 1,1, difluoroethane, 1,1,1,2 tetrafluorethane, 1,1,1,2,3,3,3-heptafluoropropane, 1,1,1,3,3,3 hexafluoropropane, ethyl acetate, acetone or combinations thereof. In another embodiment of the present invention, the volatile solvent system can include denatured alcohol, methanol, propanol, isobutene, pentane, hexane, methyl ethyl ketone, or combinations thereof. The volatile solvent system can include a mixture or combination of any of the volatile solvents set forth in the embodiments above. These volatile solvents should be chosen to be compatible with the rest of the formulation. It is desirable to use an appropriate weight percentage of the volatile solvent(s) in the formulation. Too much of the volatile solvent system prolongs the drying time. Too little of the volatile solvent system can make it difficult to spread the formulation on the skin. For most formulations, the weight percentage of the volatile solvents(s) can be from about 10 wt % to about 85 wt %, and more preferably from about 20 wt % to about 50 wt %.

The non-volatile solvent system can also be chosen or formulated to be compatible with the solidifying agent, the drug, the volatile solvent, and any other ingredients that may be present. For example, the solidifying agent can be chosen so that it is dispersible or soluble in the non-volatile solvent system. A desirable non-volatile solvent system can also act as a plasticizer for the solidifying agent. Most non-volatile solvent systems and solvent vehicles as a whole will be formulated appropriately only after experimentation. This being stated, non-volatile solvent(s) that can be used alone or in combination to form non-volatile solvent systems can be selected from a variety of pharmaceutically acceptable liquids. In one embodiment of the present invention, the non-volatile solvent system can include glycerol, propylene glycol, isostearic acid, oleic acid, propylene glycol, trolamine, tromethamine, triacetin, sorbitan monolaurate, sorbitan monooleate, sorbitan monopalmitate, or combinations thereof. In another embodiment the non-volatile solvent system can include benzoic acid, dibutyl sebecate, diglycerides, dipropylene glycol, eugenol, fatty acids such as coconut oil, fish oil, palm oil, grape seed oil, isopropyl myristate, mineral oil, oleyl alcohol, vitamin E, triglycerides, sorbitan fatty acid surfactants, triethyl citrate, or combinations thereof. In a further embodiment the non-volatile solvent system can include 1,2,6-hexanetriol, alkyltriols, alkyldiols, tocopherol, p-propenylanisole, anise oil, apricot oil, dimethyl isosorbide, alkyl glucoside, benzyl alcohol, bees wax, benzyl benzoate, butylene glycol, caprylic/capric triglyceride, caramel, cassia oil, castor oil, cinnamaldehyde, cinnamon oil, clove oil, coconut oil, cocoa butter, cocoglycerides, coriander oil, corn oil, corn syrup, cottonseed oil, cresol, diacetin, diacetylated monoglycerides, diethanolamine, diglycerides, ethylene glycol, eucalyptus oil, fat, fatty alcohols, flavors, liquid sugars ginger extract, glycerin, high fructose corn syrup, hydrogenated castor oil, IP palmitate, lemon oil, lime oil, limonene, monoacetin, monoglycerides, nutmeg oil, octyldodecanol, orange oil, palm oil, peanut oil, PEG vegetable oil, peppermint oil, petrolatum, phenol, pine needle oil, polypropylene glycol, sesame oil, spearmint oil, soybean oil, vegetable oil, vegetable shortening, wax, 2-(2-(octadecyloxy)ethoxy)ethanol, benzyl benzoate, butylated hydroxyanisole, candelilla wax, carnauba wax, ceteareth-20, cetyl alcohol, polyglyceryl, dipolyhydroxy stearate, PEG-7 hydrogenated castor oil, diethyl phthalate, diethyl sebacate, dimethicone, dimethyl phthalate, PEG Fatty acid esters such as PEG-stearate, PEG-oleate, PEG-laurate, PEG fatty acid diesters such as PEG-dioleate, PEG-distearate, PEG-castor oil, glyceryl behenate, PEG glycerol fatty acid esters such as PEG glyceryl laurate, PEG glyceryl stearate, PEG glyceryl oleate, lanolin, lauric diethanolamide, lauryl lactate, lauryl sulfate, medronic acid, multisterol extract, myristyl alcohol, neutral oil, PEG-octyl phenyl ether, PEG-alkyl ethers such as PEG-cetyl ether, PEG-stearyl ether, PEG-sorbitan fatty acid esters such as PEG-sorbitan diisosterate, PEG-sorbitan monostearate, propylene glycol fatty acid esters such as propylene glycol stearate, propylene glycol, caprylate/caprate, sodium pyrrolidone carboxylate, sorbitol, squalene, stear-o-wet, triglycerides, alkyl aryl polyether alcohols, polyoxyethylene derivatives of sorbitan-ethers, saturated polyglycolyzed C8-C10 glycerides, N-methyl pyrrolidone, honey, polyoxyethylated glycerides, dimethyl sulfoxide, azone and related compounds, dimethylformamide, N-methyl formamide, fatty acid esters, fatty alcohol ethers, alkyl-amides (N,N-dimethylalkylamides), N-methyl pyrrolidone related compounds, ethyl oleate, polyglycerized fatty acids, glycerol monooleate, glyceryl monomyristate, glycerol esters of fatty acids, silk amino acids, PPG-3 benzyl ether myristate, Di-PPG2 myreth 10-adipate, honeyquat, sodium pyroglutamic acid, abyssinica oil, dimethicone, macadamia nut oil, lirnnanthes alba seed oil, cetearyl alcohol, PEG-50 shea butter, shea butter, aloe vera juice, phenyl trimethicone, hydrolyzed wheat protein, or combinations thereof. In yet a further embodiment the nonvolatile solvent system can include a combination or mixture of non-volatile solvents set forth in the any of the above discussed embodiments.

In addition to these and other considerations, the non-volatile solvent system can also serve as plasticizer in the adhesive formulation so that when the solidified layer is formed, the layer is flexible, stretchable, and/or otherwise "skin friendly."

Certain volatile and/or nonvolatile solvent(s) that are irritating to the skin may be desirable to use to achieve the desired solubility and/or permeability of the drug. It is also desirable to add compounds that are both capable of preventing or reducing skin irritation and are compatible with the formulation. For example, in a formulation where the non-volatile and/or volatile solvent is capable of irritating the skin, it would be helpful to use a non-volatile solvent that is capable of reducing skin irritation. Examples of non-volatile solvents that are known to be capable of preventing or reducing skin irritation include, but are not limited to, glycerin, honey, and propylene glycol.

The formulations of the current invention may also contain ion-paring agents such as bases and acids. The purpose of these agent(s) can be to optimize the ionization state of the drug for obtaining desired delivery rates or to optimize the pH of the formulation or the skin tissues under the formulation layer to minimize irritation. Examples of suitable ion-pairing agents include, but are not limited to, trolamine, hydrochloric acid, sodium hydroxide, and/or acidic acid.

The selection of the solidifying agent can also be carried out in consideration of the other components present in the adhesive formulation. An appropriate solidifying agent is compatible with the formulation such that the formulation is in liquid or semi-liquid state (e.g. cream, paste, gel, ointment) without phase separation and without lumps or precipitation before any evaporation of the volatile solvent(s) and becomes a soft, coherent solid after the evaporation of at least some of the volatile solvent(s). The solidifying agent can be selected or formulated to be compatible to the drug and the solvent vehicle (including the volatile solvent(s) and the non-volatile solvent system), as well as provide desired physical properties to the solidified layer once it is formed. Depending on the drug, solvent vehicle, and/or other components that may be present, the solidifying agent can be selected from a variety of agents.

In one embodiment, the solidifying agent can include polyvinyl alcohol with a MW range of 20,000-70,000 (Amresco), esters of polyvinylmethylether/maleic anhydride copolymer (ISP Gantrez ES-425 and Gantrez ES-225) with a MW range of 80,000-160,000, neutral copolymer of butyl methacrylate and methyl methacrylate (Degussa Plastoid B) with a MW range of 120,000-180,000, dimethylaminoethyl methacrylate-butyl methacrylate-methyl methacrylate copolymer (Degussa Eudragit E100) with a MW range of 100,000-200,000, ethyl acrylate-methyl methacrylate-trimethylammonioethyl methacrylate chloride copolymer with a MW greater than 5,000 or similar MW to Eudragit RLPO (Degussa), Zein (prolamine) with a MW greater than 5,000 such as Zein with a MW around 35,000 (Freeman industries), pregelatinized starch having a MW similar to Instant Pure-Cote B793 (Grain Processing Corporation), ethyl cellulose with a MW greater than 5,000 or a MW similar to Aqualon EC N7, N10, N14, N22, N50, or N100 (Hercules), fish gelatin having a MW 20,000-250,000 (Norland Products), gelatin, other animal sources with a MW greater than 5,000, acrylates/octylacrylamide copolymer with a MW greater than 5,000 or MW similar to National Starch, and/or Chemical Dermacryl 79.

In another embodiment, the solidifying agent can include ethyl cellulose, hydroxy ethyl cellulose, hydroxy methyl cellulose, hydroxy propyl cellulose, hydroxypropyl methyl cellulose, carboxymethyl cellulose, methyl cellulose, polyether amides, corn starch, pregelatinized corn starch, polyether amides, shellac, polyvinyl pyrrolidone, polyisobutylene rubber, polyvinyl acetate phthalate, or combinations thereof. In a further embodiment the solidifying agent can include ammonia methacrylate, carrageenan, cellulose acetate phthalate aqueous such as CAPNF from Eastman, carboxy polymethylene, cellulose acetate (microcrystalline), cellulose polymers, divinyl benzene styrene, ethylene vinyl acetate, silicone, guar gum, guar rosin, gluten, casein, calcium caseinate, ammonium caseinate, sodium caseinate, potassium caseinate, methyl acrylate, microcrystalline wax, polyvinyl acetate, PVP ethyl cellulose, acrylate, PEG/PVP, xantham gum, trimethyl siloxysilicate, maleic acid/anhydride colymers, polacrilin, poloxamer, polyethylene oxide, poly glactic acid/poly-l-lactic acid, turpene resin, locust bean gum, acrylic copolymers, polyurethane dispersions, dextrin, polyvinyl alcohol-polyethylene glycol co-polymers, methyacrylic acid-ethyl acrylate copolymers such as BASF's Kollicoat polymers, methacrylic acid and methacrylate based polymers such as poly(methacrylic acid), or combinations thereof. In another embodiment, the solidifying agent can include a combination of solidifying agents set forth in the any of the above discussed embodiments. Other polymers may also be suitable as the solidifying agent, depending on the solvent vehicle components, the drug, and the specific functional requirements of the given formulation. Other polymers may also be suitable as the solidifying agent, depending on the solvent vehicle components, the drug, and the specific functional requirements of the given formulation.

The selection of the peel-forming agent can also be carried out in consideration of the other components present in the adhesive peelable formulation. The peel-forming agent can be selected or formulated to be compatible to the drug and the solvent vehicle (including the volatile solvent(s) and the non-volatile solvent system), as well as to provide desired physical properties to the solidified peelable layer once it is formed. Depending on the drug, solvent vehicle, and/or other components that may be present, the peel-forming agent can be selected from a variety of agents, including but not limited to polyethylene oxide, ammonia methacrylate, carrageenan, cellulose acetate phthalate aqueous such as CAPNF from Eastman, carboxy methyl cellulose Na, carboxy polymethylene, cellulose, cellulose acetate (microcrystalline), cellulose polymers, divinyl benzene styrene, ethyl cellulose, ethylene vinyl acetate, silicone, polyisobutylene, shellac (FMC BioPolymer), guar gum, guar rosin, cellulose derivatives such as hydroxy ethyl cellulose, hydroxy methyl cellulose, hydroxy propyl cellulose, hydroxypropyl methyl cellulose, carboxymethyl cellulose, and methyl cellulose, hypromellose phthalate (hydroxypropyl methylcellulose phthalate), methyl acrylate, microcrystalline wax, polyvinyl alcohol, polyvinyl acetate, polyvinyl acetate phthalate such as Suretic from Colorcon, PVP ethyl cellulose, polyvinyl yrrolidone (PVP), acrylate, PEG/PVP, xantham Gum, trimethyl siloxysilicate, maleic acid/anhydride copolymers!, polacrilin, poloxamer, polyethylene oxide, poly glactic acid /poly-l-lactic acid, turpene resin, locust bean gum, prolamine (Zein), acrylic copolymers, polyurethane dispersions, gelatin, dextrin, starch, polyvinyl alcohol-polyethylene glycol co-polymers, methyacrylic acid-ethyl acrylate copolymers such as BASF's Kollicoat polymers, methacrylic acid and methacrylate based polymers such as poly(methacrylic acid) copolymers and methylmethacrylate copolymers, including Rohm and Haas' Eudragit polymers (Eudragit (E, L, NE, RL, RS, S100)), Esters of polyvinylmethylether/maleic anhydride copolymer such as Gantrez ES-425, Gantrez ES-225 available from ISP, and mixtures thereof. Other film forming polymers may also be suitable as the peel-forming agent, depending on the solvent vehicle components, the drug, and the specific functional requirements of the given formulation.

In some embodiments of the present invention, it may be desirable to add an additional agent or substance to the formulation so as to provide enhanced or increased adhesive characteristics. The additional adhesive agent or substance can be an additional non-volatile solvent or an additional solidifying agent. Non-limiting examples of substances which might be used as additional adhesion enhancing agents include copolymers of methylvinyl ether and maleic anhydride (Gantrez polymers), polyethylene glycol and polyvinyl pyrrolidone, gelatin, low molecular weight polyisobutylene rubber, copolymer of acrylsan alkyl/octylacrylamido (Dermacryl 79), various aliphatic resins and aromatic resins, and combinations thereof.

The non-volatile solvent system and the solidifying agent should be compatible with each other. Compatibility can be defined as i) the solidifying agent does not substantially negatively influence the function of the non-volatile solvent system, though some reduction of flux may be acceptable; ii) the solidifying agent can hold the non-volatile solvent system in the solidified layer so that substantially no non-volatile solvent oozes out of the layer, and/or iii) the solidified layer formed with the selected non-volatile solvent system and the solidifying agent has acceptable flexibility, rigidity, tensile strength, elasticity, and adhesiveness. The weight ratio of the non-volatile solvent system to the solidifying agent can be from about 0.1:1 to about 10:1. In another aspect, the ratio between the non-volatile solvent system and the solidifying agent can be from about 0.5:1 to about 2:1.

The thickness of the formulation layer applied on the skin should also be appropriate for a given formulation and desired drug delivery considerations. If the layer is too thin, the amount of the drug may not be sufficient to support sustained delivery over the desired length of time. If the layer is too thick, it may take too long to form a non-messy outer surface while the solidified layer is forming. If the drug is very potent and the peel has very high tensile strength, a layer as thin as about 0.01 mm may be sufficient. If the drug has rather low potency and the solidified layer has low tensile strength, a layer as thick as about 2-3 mm maybe needed. Thus, for most drugs and formulations, the appropriate thickness can be from about 0.01 mm to about 3 mm, but more typically, from about 0.05 mm to about 1 mm.

The flexibility and stretchability of a solidified layer, which is optionally peelable, can be desirable in some applications. For instance, the formulation may be used to treat a skin area that is suffering from neuropathic pain and is directly over joints and muscles. Skin areas over joints and certain muscle groups are often significantly stretched during body movements. Such movement prevents non-stretchable patches from maintaining good skin contact. Lotions, ointments, creams, gels, pastes, or the like also may not be suitable for use for the reasons cited above. As such, a flexible, elastic solidified layer will be desirable in these applications can offer unique advantages and benefits. It should be pointed out that although good stretchability can be desirable in many applications, the solidifying formulations of the present invention do not always need to be stretchable, as certain applications of the present invention do not necessarily benefit from this property and these solidified layers are also included in accordance with embodiments of the present invention.

A further feature of the formulations of the present invention is related to the drying time. If a formulation dries too quickly, the user may not have sufficient time to spread the formulation into a thin layer on the skin surface before the formulation is solidified, leading to poor skin contact. If the formulation dries too slowly, the user may have to wait a long time before resuming normal activities (e.g. putting clothing on) that may remove un-solidified formulation. Thus, it is desirable for the drying time to be longer than about 15 seconds but shorter than about 15 minutes, and preferably from about 0.5 minutes to about 5 minutes.

Another feature of the formulations of the present invention is related to solidifying formulations comprising a drug for controlling neuropathic pain, a non-volatile solvent system comprising at least one non-volatile solvent, a solidifying agent, and a volatile solvent system comprising a volatile solvent whose boiling point is below 20° C. (such a solvent can be used as a propellant or can be dissolved in the formulation). In one embodiment, the formulation can be stored in a pressurized container and be sprayed on the skin surface with the help of the propellant. Some hydrofluorocarbons commonly used as propellants in pharmaceutical or dosmetic industries can work in this design. More specifically, the propellants may include, but not limited to dimethyl ether, butane, 1,1, Difluoroethane, 1,1,1,2 tetrafluorethane, 1,1,1,2, 3,3,3-heptafluoropropane, 1,1,1,3,3,3 hexafluoropropane, or a mixture thereof. The formulation may also be expelled out of the container and applied on the skin via a manual pump. Formulations comprising a these room temperature gaseous volatile solvents are expected to dry much faster. Spraying the formulation onto the skin suffering from neuropathic pain can avoid touching the skin with an applicator which can cause severe pain in the sometimes hypersensitive skin.

The formulations of the current invention may further comprise a pH modifying agent for adjusting the pH of the formulation to a point or a range most suitable for the delivery of the drug. This feature can be important for a drug that is ionizable.

Other benefits of the solidified layers of the present invention include the presence of a physical barrier that can be formed by the material itself. Since many subjects suffering from neuropathic pain feel tremendous pain when their skin area is touched with minimal pressure, the physical barrier of the solidified layer can prevent or minimize pain caused by accidental contact.

The adhesion to skin and elasticity of the material is such that the solidified layer may not easily separate from the skin. For example, in one embodiment, the solidified layer can be stretched in at least one direction by up to about 5% or even 10% or more without cracking, breaking, or separating form a skin surface to which the solidified layer is applied.

These and other advantages can be summarized as follows. The solidifying formulation of the present invention can be in an initial form that is easy to apply as a semisolid dosage form. Additionally, upon volatile solvent system evaporation, the dosage form is relatively thick and can contain much more active drug than a typical layer of traditional cream, gel, lotion, ointment, paste, etc., and further, is not as subject to unintentional removal. After the evaporation of the volatile solvent(s) and the formation of the solidified layer, the drug in the remaining formulation can be delivered at desired delivery rates over sustained periods of time. Further, as the solidified layer remains adhered to skin and is preferably peelable, easy removal of the solidified layer can occur, usually without the aid of a solvent or surfactant. In some embodiments, the non-volatile solvent system is so selected or formulated that it is flux-enabling for the drug. In some embodiments, the adhesion to skin and elasticity of the material is such that the solidified layer will not separate from the skin upon skin stretching at highly stretchable skin areas, such as over joints and muscles. For example, in one embodiment, the solidified layer can be stretched to 10% or greater in one direction without cracking, breaking, and/or separating form a skin surface to which the solidified layer is applied. Still further, the solidified layer can be configured to advantageously deliver drug and protect sensitive skin areas without cracking or breaking.

As a further note, it is a unique feature that the solidified layers of the present invention can keep a substantial amount of the non-volatile solvent system, which is optimized for delivering the drug, on the body surface. This feature can provide unique advantages over existing products. For example, in some semi-solid formulations, upon application to a skin surface the volatile solvents quickly evaporate and the formulation layer solidifies into a hard lacquer-like layer. The drug molecules are immobilized in the hard lacquer layer and are substantially unavailable for delivery into the skin surface. As a result, it is believed that the delivery of the drug is not sustained over a long period of time. In contrast to this type of formulation, the solidified layers formed using the formulations of the present invention keep the drug molecules quite mobile in the non-volatile solvent system which is in contact with the skin surface, thus ensuring sustained delivery.

Specific examples of applications that can benefit from the systems, formulations, and methods of the present invention are as follows. In one embodiment, a solidified layer including bupivacaine, lidocaine, tetracaine or ropivacaine, or a mixture thereof, can be formulated for treating diabetic and post herpetic neuralgia. Alternatively, dibucanine and/or an alpha-2 agonist such as clonidine can be formulated in a solidified layer for treating the same disease. Solidifying formulations containing antiviral drugs such as acyclovir, penciclovir, famciclovir, valacyclovir, steroids, or behenyl alcohol can be formulated for treating herpes viral infections, the underlying cause for certain neuropathic pain.

Another embodiment entails a solidifying formulation containing a drug from the class of alpha-2 antagonists which is applied topically to treat neuropathic pain. The alpha-2 agonist is gradually released from the formulation to provide pain relief over a sustained period of time. The formulation can become a coherent, soft solid and remains adhered to the body surface for the length of its application. It is easily removed after drying without leaving residual formulation on the skin surface.

Another embodiment involves a formulation containing capsaicin which is applied topically to treat neuropathic pain. The capsaicin is gradually released from the formulation for treating this pain over a sustained period of time. The formulation can become a coherent, soft solid and remain adhered to the body surface for the length of its application. It is easily removed any time after drying without leaving residual formulation on the skin surface.

A further embodiment involves a solidified formulation containing at least one alpha-2 agonist drug, at least one tricyclic antidepressant agent, and/or at least one local anesthetic drug which is applied topically to treat neuropathic pain. The drugs are gradually released from the formulation to provide pain relief over a sustained period of time. The formulation can become a coherent, soft solid and remain adhered to the body surface for the length of its application. It is easily removed any time after drying without leaving residual formulation on the skin surface.

In another embodiment, the delivery of drugs for treating neuropathic pain can also benefit from the methods, systems, and formulations of the present invention. A patch containing a local anesthetic agent is used for treating neuropathic pain, such as pain caused by post-herpetic neuralgia. Due to the limitations of the patch as discussed above, a solidified layer prepared in accordance with the present invention provides some unique benefits, as well as provide a potentially less expensive alternative to the use of such a patch. Possible drugs delivered for such applications include, but are not limited to, local anesthetics such as lidocaine, prilocalne, tetracaine, bupivicaine, etidocaine; and other drugs including ketamine, amitriptyline, capsaicin, tricyclic antidepressants, alpha-2 agonists such as clonidine, or combinations thereof.

In one embodiment, the drug can be an antiviral agent and the solidified layer is capable of generating a flux of the antiviral agent of at least 2 mcg/cm$^2$/h. In another embodiment, the drug can be a local anesthetic and the solidified layer is capable of generating a flux of the local anesthetic of at least 5 mcg/cm$^2$/h. In another embodiment, the drug can be an alpha-2 agonist and the solidified layer is capable of generating a flux of the alpha-2 agonist of at least 1 mcg/cm$^2$/h. In another embodiment, the drug is capsaicin and the solidified layer is capable of generating a flux of capsaicin of at least 5 mcg/cm$^2$/h. In yet a further embodiment, the drug is ketamine and the solidified layer is capable of generating a flux of ketamine of at least 1 mcg/cm$^2$/h.

Solidifying formulations of the current invention that comprise two or more active drugs may provide additional benefits. For example, a formulation for treating neuropathic pain in accordance with the current invention may include lidocaine and tetracaine. The lidocaine and tetracain can be present in either the salt form or in the base form. Preferably, the non-volatile solvent system includes at least one of propylene glycol and dipropylene glycol, and isostearic acid. Similar formulations may comprise other combinations of drugs, such as amitriptyline and ketamine, amitriptyline and a local anesthetic, etc.

EXAMPLES

The following examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. The appended claims are intended to cover such modifications and arrangements. Thus, while the present invention has been described above with particularity, the following examples provide further detail in connection with what are presently deemed to be the most practical and preferred embodiments of the invention.

Example 1

Hairless mouse skin (HMS) or human epidermal membrane (HEM) is used as the model membranes as noted for the in vitro flux studies described in herein. Hairless mouse skin (HMS) is used as the model membrane for the in vitro flux studies described in herein. Freshly separated epidermis removed from the abdomen of a hairless mouse is mounted carefully between the donor and receiver chambers of a Franz diffusion cell. The receiver chamber is filled with pH 7.4 phosphate buffered saline (PBS). The experiment is initiated by placing test formulations on the stratum corneum (SC) of the skin sample. Franz cells are placed in a heating block maintained at 37° C. and the HMS temperature is maintained at 35° C. At predetermined time intervals, 800 μL aliquots are withdrawn and replaced with fresh PBS solution. Skin flux (µg/cm²/h) is determined from the steady-state slope of a plot of the cumulative amount of permeation versus time. It is to be noted that human cadaver skin can be used as the model membrane for the in vitro flux studies as well. The mounting of the skin and the sampling techniques used as the same as described above for the HMS studies.

Example 2

Formulations of ropivacaine (base) in various non-volatile solvent systems are evaluated. Excess ropivacaine is present. The permeation of ropivacaine from the test formulations through HMS is presented in Table 2 below.

TABLE 2

| Non-volatile solvent system | Skin Flux* (mcg/cm²/h) |
|---|---|
| Glycerol | 1.2 ± 0.7 |
| Tween 20 | 2.4 ± 0.1 |
| Mineral Oil | 8.9 ± 0.6 |
| ISA (Isostearic Acid) | 11 ± 2 |
| Span 20 | 26 ± 8 |

*Skin flux measurements represent the mean and standard deviation of three determinations. Flux measurements reported were determined from the linear region of the cumulative amount versus time plots. The linear region was observed to be between 4-8 hours. If experimental conditions allowed, the steady-state delivery would likely continue well beyond 8 hours.

Steady state flux of ropivacaine base from the above non-volatile solvents are obtained by placing 200 mcL on the stratum corneum side (donor) of hairless mouse skin. The in vitro studies are carried out as described in Example 1. It is estimated that for treating skin neuropathic pain, the flux needs to be above about 5-10 µg/cm²/h. The range in ropivacaine flux values from the above non-volatile solvents illustrates that some solvents (Span 20, possibly mineral oil) are likely "flux-enabling" non-volatile solvents.

Examples 3-5

Three formulations containing ropivacaine HCl are applied on the stratum corneum side of freshly separated hairless mouse skin. The in vitro flux is determined for each formulation as outlined in Example 1. The formulation compositions are noted in Table 3 below.

TABLE 3

| | Example | | |
|---|---|---|---|
| | 3 | 4 | 5 |
| | % by weight | | |
| PVA | 15 | 15 | 15 |
| Water | 23 | 23 | 23 |
| Ethylcellulose N-100 | 11 | 11 | 11 |
| Ethanol | 33 | 33 | 33 |
| Span 20 | 11 | | |
| Polyethylene Glycol 400 | | 11 | |
| Tween 40 | | | 11 |
| Tromethamine | 4 | 4 | 4 |
| Ropivacaine HCl | 3 | 3 | 3 |
| Avg. Flux* (mcg/cm²/h) | 15 ± 1 | 4.7 ± 0.3 | 3.4 ± 0.7 |

*Flux values represent the mean and standard deviation of three determinations. Flux measurements reported were determined from the linear region of the cumulative amount versus time plots. The linear region was observed to be between 4-9 hours. If the experiment was continued it is anticipated the steady state would continue.

Since all three formulations have the exact same compositions of solidifying agent, volatile solvents, and flux-enabling non-volatile solvent. The only difference is in the non-volatile solvent system. It is reasonable to conclude that for ropivacaine HCl that the non-volatile solvent system in Example 3 is flux-enabling.

Examples 6-7

A peel-forming formulation for dermal delivery of ropivacaine is prepared which includes a specified amount of ropivacaine in an excipient mixture to form an adhesive peelable formulation in accordance with embodiments of the present invention. The peel formulations contained the following components:

TABLE 4

Ropivacaine peelable formulation ingredients.

| | Examples | |
|---|---|---|
| Ingredients* | 6 | 7 |
| Eudragit RL-100 | 39.6% | 39.6% |
| Ethanol | 23.7% | 23.6% |
| ISA (Isostearic Acid) | 13.5% | 13.5% |
| PG (Propylene Glycol) | 7.9% | 4.0% |
| Trolamine | 4.0% | 4.0% |
| Glycerol | 7.9% | 11.9% |
| Ropivacaine | 3.4% | 3.4% |

*Ingredients are noted as weight percent.

Formulations of Examples 6 and 7 are prepared in the following manner:
  The solidifying agent is dissolved in the volatile solvent,
  The non-volatile solvent is mixed with the solidifying agent/volatile solvent mixture.
  The resulting solution is vigorously mixed well for several minutes.
  The drug is then added and the formulation is mixed again for several minutes.

In the formulations noted above, the non-volatile solvent/solidifying agent/volatile solvent combination is compatible as evidenced by a homogeneous, single phase system that exhibited appropriate drying time, and provided a stretchable peel and steady state flux for the drug. These formulations are applied to HMS skin as described in Example 1, and the ropivacaine flux is measured. A summary of the results from in vitro flux studies carried out with the formulations in Examples 6 and 7 is listed in Table 5.

TABLE 5

Steady-state flux of Ropivacaine through hairless mouse skin from various adhesive peelable formulations at 35° C.

| Formulation | Average flux mcg/cm²/h* |
|---|---|
| Example 6 | 36 ± 5 |
| Example 7 | 32 ± 2 |

*The flux values represent the mean and SD of three

Regarding the formulation described in Examples 6 and 7, ethanol is used as the volatile solvent, and the ISA, glycerol, and PG mixture is used as the flux enabling non-volatile solvent system. Through experimentation, it is determined that ISA and propylene glycol used together to provide the appropriate solubility and flux for the drug, while being compatible with the Eudragit RL-100 solidifying agent. Further, in this embodiment, ISA, PG and glycerol serve as a plasticizer in the peelable formulation after the ethanol (volatile solvent) has evaporated.

Example 8

The effect of solubility on permeation, compatibility between the non-volatile solvent system and the solidifying agent is shown in this example. Ropivacaine base solubility in isostearic acid (ISA) is experimentally determined to be slightly above 1:4, meaning 1 gram ropivacaine base can completely dissolve in 4 gram isostearic acid. In one experiment, two solutions are made: Solution A includes 1 part ropivacaine base and 4 parts isostearic acid. Solution B includes 1 part ropivacaine base, 4 parts isostearic acid, and 1 part trolamine. (all parts are in weight). All ropivacaine in Solution A is dissolved, but only a portion of ropivacaine in solution B is dissolved. The transdermal flux across hairless mouse skin generated by the solutions is measured by a typical Franz Cell system similar to that in Example 1, with the following results:

TABLE 6

Flux across hairless mouse skin, in vitro, in μg/hr/cm²

|            | Cell 1 | Cell 2 | Cell 3 | Average |
|------------|--------|--------|--------|---------|
| Solution A | 13.1   | 9.9    | 9.1    | 10.7    |
| Solution B | 43.2   | 35.0   | 50.0   | 42.7    |

As can be seen, the flux generated by Solution B is about 4 times that of Solution A. These results demonstrate that the addition of the ion paring agent (pH modifying agent) trolamine significantly increases the transdermal flux. However, the attempt to incorporate this system into a poly vinyl alcohol (PVA) based solidifying formulation failed because the PVA in the formulation acted as a strong pH buffer that inhibited the effect of trolamine. Addition of more trolamine, in attempt to over-power the pH buffer capacity of PVA, caused the loss of the desired solidifying property of PVA (in other words, a non-volatile solvent system containing ISA and too much trolamine is not compatible with PVA). When PVA is replaced by another solidifying agent, Eudragit RL 100 (Rohm & Haas), the effect of trolamine is not inhibited and formulations capable of generating fluxes around 30 μg/hr/cm² were obtained. A by product of the addition of trolamine, ISA, and Eudragit RL 100 is that a precipitate forms from the ionic interaction of the three components. The latter Example produced a better formulation in terms of flux and wear properties, but the precipitation still demonstrates the need for improvement. In an effort to eliminate the ionic interaction between non-volatile solvent and solidifying agent the trolamine, ISA mixture was added to Plastoid B polymer in isopropanol. However, in this instance the trolamine was found to be incompatible with the Plastoid B polymer and the base was changed to triisopropanolamine. This combination eliminated the precipitate formed when the Eudragit RL 100 polymer was used and produced a clear formulation that was capable of generated flux values around 30 μg/hr/cm². This demonstrates the importance of compatibility between the non-volatile solvent system and the solidifying agent.

Example 9

A solidifying formulation for dermal delivery of ropivacaine is prepared from the following ingredients:

TABLE 7

Ropivacaine solidifying formulation components

| Ingredients*    | Example 13 |
|-----------------|------------|
| Ropivacaine HCl | 0.096      |
| Eudragit RL-100 | 1.0        |
| Ethanol         | 0.7        |
| Isostearic Acid | 0.34       |
| Glycerol        | 0.3        |
| Propylene Glycol| 0.1        |
| Trolamine       | 0.15       |

*Ingredients are noted as parts by weight.

The ingredients listed above are combined according to the following procedure. The Eudragit RL-100 and ethanol are combined in a glass jar and heated to about 60° C. until the Eudragit RL-100 is completely dissolved. Once the Eudragit solution cooled to room temperature, the appropriate amount of ropivacaine HCl is added and mixed thoroughly for 1 minute. To this solution, isostearic acid (ISA) is added and the mixture is stirred vigorously for 2-3 minutes. One hour later, the solution is vigorously mixed again for 2-3 minutes. To this solution, glycerol, propylene glycol, and trolamine are added in sequential order. After addition of each ingredient the solution is stirred for 1 minute.

Example 10

The formulation prepared in accordance with Example 9 is applied to HMS as described in Example 1, and the ropivacaine flux was measured. A summary of the results is listed in Table 8, as follows:

TABLE 8

Steady-state flux of ropivacaine through hairless mouse skin from various adhesive peelable formulations at 35° C.

| Formulation | Average flux mcg/cm²/h* |
|-------------|-------------------------|
| Example 9   | 43 ± 4                  |

*The flux values represent the mean and SD of three determinations

The ropivacaine peel formulation prepared in accordance with Example 9 possessed acceptable application properties, e.g., ease of removal of peel from the sample tube, ease of spreading on intended skin application site, etc., and forms a solidified film in 2-3 minutes after being applied to normal human skin surface as a thin layer with a thickness of about 0.1 mm. The solidified layer becomes more easily peelable in 2 hours, and the peel remains affixed to the skin surface without any unintended removal of the solidified layer for at least 12 hours. At the end of intended use, the solidified layer is easily removed in one continuous piece.

Example 11

A solidifying formulation for dermal delivery of lidocaine is prepared which includes a saturated amount of lidocaine (base) in an excipient mixture to form an adhesive solidifying formulation in accordance with embodiments of the present invention. The formulation is prepared from the ingredients as shown in Table 9.

TABLE 9

Lidocaine solidifying formulation components.

| Ingredients* | Example 15 |
|---|---|
| PVA | 11.7 |
| Eudgragit E-100** | 11.7 |
| PVP-K90 | 5.8 |
| Glycerol | 8.8 |
| PEG-400 | 8.8 |
| Water | 23.8 |
| Ethanol | 23.8 |
| Lidocaine | 5.6 |

*Ingredients are noted as weight percent.
**from Rohm & Haas

TABLE 10

Steady-state flux of lidocaine through hairless mouse skin from various adhesive solidifying formulations at 35° C.

| Formulation | Average flux mcg/cm$^2$/h* |
|---|---|
| Example 11 | 47 ± 3 |

The formulation in the present Example has similar physical properties to the formulations in Examples noted above. The transdermal flux across hairless mouse skin is likely acceptable and steady-state delivery is maintained over 8 hours.

Examples 12-15

Solidifying formulations for dermal delivery of amitriptyline and a combination of amitripyline and ketamine are prepared which include excipient mixtures to form an adhesive solidifying formulation in accordance with embodiments of the present invention. The formulations are prepared from the ingredients as shown in Table 11.

TABLE 11

Amitriptyline and amitriptyline/ketamine solidifying formulation components

| | Example | | | |
|---|---|---|---|---|
| Ingredients* | 12 | 13 | 14 | 15 |
| Isopropanol | 50.3 | 48.6 | 50.8 | 49.8 |
| Water | 2.7 | 2.6 | 2.7 | 2.7 |
| Isostearic Acid | 6.2 | 6.1 | 6.3 | 6.2 |
| Triisopropanolamine | 7.5 | 7.3 | 7.5 | 7.4 |
| Triacetin | 2.9 | 2.8 | 2.9 | 2.8 |
| Span 20 | 5.7 | 5.5 | 5.8 | 5.6 |
| Plastoid B** | 21.7 | 21.1 | 22 | 21.5 |
| Amitriptyline | 2 | 4 | | |
| Ketamine | 1 | 2 | 2 | 4 |

*Ingredients are noted as weight percent.
**from DeGussa.

The ingredients listed above are combined according to the following procedure. The drug(s), water, and triisopropanolamine are combined in a glass jar and mixed until the drug is dissolved. Then the isostearic acid, triacetin, Span 20, and isopropanol are added to the formulation and mixed well. The polymer Plastoid B is added last and heated to about 60° C. until the Plastoid B is completely dissolved. Once the polymer solution cooled to room temperature, the formulation is stirred vigorously for 2-3 minutes.

The formulations in Table 11 are applied to HMS according to Example 1, and the flux of amitriptyline and/or ketamine was measured. The results are summarized in Table 12:

TABLE 12

Steady-state flux of amitriptyline and amitriptyline/ketamine through hairless mouse skin from various adhesive solidifying formulations at 35° C.

| Formulation | Average amitriptyline flux mcg/cm$^2$/h* | Average ketamine flux mcg/cm$^2$/h* |
|---|---|---|
| Example 12 | 3 ± 1 | 15 ± 4 |
| Example 13 | 7.6 ± 0.2 | 38 ± 6 |
| Example 14 | 3 ± 1 | |
| Example 15 | 8.2 ± 0.7 | |

The adhesive formulation of amitriptyline and amitriptyline/ketamine formulations in the present example have similar physical properties to the formulations in examples noted above.

Examples 16-19

Solidifying formulations for dermal delivery of ropivacaine HCl are prepared which include excipient mixtures in accordance with embodiments of the present invention. The formulations are prepared from the ingredients as shown in Table 13.

TABLE 13

Ropivacaine HCl solidifying formulation components.

| | Example | | | |
|---|---|---|---|---|
| Ingredients* | 16 | 17 | 18 | 19 |
| Ropivacaine HCl | 0.31 | 0.31 | 0.31 | 0.31 |
| Isopropanol | 2 | 2 | 2.2 | 2 |
| Water | 0.125 | 0.125 | 0.125 | 0.125 |
| Isostearic Acid | 0.36 | 0.66 | 0.41 | 0 |
| Triisopropanolamine | 0.31 | 0.34 | 0.34 | 0.34 |
| Triacetin | 0.17 | 0.19 | 0 | 0.19 |
| Span 20 | 0.34 | 0 | 0.37 | 0.66 |
| Plastoid B** | 1 | 1 | 1 | 1 |

*Ingredients are noted as parts by weight.
**from Degussa.

The ingredients listed above are combined according to the following procedure. The ropivacaine HCl, water, and triisopropanolamine are combined in a glass jar and mixed until the drug is dissolved. Then the isostearic acid, triacetin, Span 20, and isopropanol are added to the formulation and mixed well. The polymer Plastoid B is added last and heated to about 60° C. until the Plastoid B is completely dissolved. Once the polymer solution cooled to room temperature, the formulation is stirred vigorously for 2-3 minutes.

The formulations in Table 13 are applied to HMS according to Example 1, and the flux of ropivacaine was measured. The results are summarized in Table 14:

TABLE 14

Steady-state flux of ropivacaine HCl through hairless mouse skin from various adhesive solidifying formulations at 35° C.

| Formulation | Average flux mcg/cm²/h* |
|---|---|
| Example 16 | 56 ± 2 |
| Example 17 | 39 ± 6 |
| Example 18 | 31 ± 6 |
| Example 19 | 37 ± 9 |

The flux of Examples 16-19 shows the importance of the triacetin, isostearic acid, Span 20 combination in the formulation. In Examples 17-19 formulations are made without Span 20, triacetin, and isostearic acid respectively. The flux of ropivacaine is impacted. The synergistic combination of the non volatile solvents is an important in obtaining the maximum flux of ropivacaine.

Example 20

This solidifying formulation has the following ingredients in the indicated weight parts:

TABLE 15

| PVA | Water | Ethyl Cellulose N-7 (Aqualon) | Dermacryl 79 (National Starch) | Ethanol | Isostearic Acid (ISA) | Glycerol | Ropivacaine |
|---|---|---|---|---|---|---|---|
| 1 | 1.5 | 0.25 | 0.35 | 0.85 | 0.8 | 0.35 | 0.3 |

In this formulation, polyvinyl alcohol (USP grade, mw 31,000-50,000, from Amresco) is a solidifying agent, ethyl cellulose and Dermacryl 79 are auxiliary solidifying agents. Isostearic acid and glycerol form the non-volatile solvent system while ethanol and water form the volatile solvent system. Ropivacaine is the drug.

Procedures of making the formulation:
1. Ropivacaine is mixed with ISA.
2. Ethyl cellulose and Dermacryl 79 are dissolved in ethanol.
3. PVA is dissolved in water at temperature of about 60-70 C.
4. All of the above mixtures are combined together in one container and glycerol is added and the whole mixture is mixed well.

The resulting formulation is a viscous fluid. When a layer of about 0.1 mm thick is applied on skin, a non-tacky surface is formed in less than 2 minutes.

Example 21

A formulation similar to the formulation of Example 11 composition (with no lidocaine) is applied onto a human skin surface at an elbow joint and a finger joint, resulting in a thin, transparent, flexible, and stretchable film. After a few minutes of evaporation of the volatile solvents (ethanol and water), a solidified layer is formed. The stretchable film has good adhesion to the skin and does not separate from the skin on joints when bent, and can easily be peeled away from the skin.

Example 22

A number of non-volatile solvents are tested for their flux-enabling ability for dermal delivery of tetracaine. Each of the solutions in the table below contain saturated amounts of tetracaine base. The transdermal flux of tetracaine generated by the saturated solutions are measured by a setup similar to that in Example 1. The results are as follows:

TABLE 16

| Non-volatile solvent | Flux (µg/cm²/h) |
|---|---|
| Glycerin | 3.8 ± 2.9 |
| Isostearic acid | 60.5 ± 15.3 |
| Propylene Glycol | 83.9 ± 11 |
| Triacetin | 5.7 ± 0.7 |

The importance of selecting a non-volatile solvent system to achieving therapeutically effective dermal drug flux is clearly shown here.

Examples 23-25

Solidifying formulations for dermal delivery of ropivacaine HCl are prepared which include excipient mixtures in accordance with embodiments of the present invention. The formulations are prepared from the ingredients as shown in Table 17.

TABLE 17

Ropivacaine HCl solidifying formulation components

| Ingredients* | Example 23 | Example 24 | Example 25 |
|---|---|---|---|
| Ropivacaine HCl | 6.9 | 6.5 | 6.6 |
| Isopropanol | 50.7 | 45.8 | 45.9 |
| Water | 5.5 | 5.2 | 5.2 |
| Isostearic Acid | 6.3 | 6.6 | 6.6 |
| Triethylamine | | | 3.0 |
| Diisopropanolamine | | 3.9 | |
| Cetyl alcohol | | 3.3 | 3.9 |
| Triacetin | 2.9 | 2.6 | 2.6 |
| Span 20 | 5.8 | 5.2 | 5.2 |
| Plastoid B** | 21.9 | 20.9 | 21.0 |

*Ingredients are noted as weight percent.
**from Degussa.

The ingredients listed above are combined according to the following procedure. The ropivacaine HCl, water, and the amine base (triethylamine or diisopropanolamine) are combined in a glass jar and mixed until the drug is dissolved. Then, the isostearic acid, triacetin, Span 20, and cetyl alcohol (Examples 24 and 25) or isopropanol (Example 23) is added to the formulation and mixed well. The polymer Plastoid B is added last and heated to about 60° C. until the Plastoid B is completely dissolved. Once the polymer solution cooled to room temperature, the formulation is stirred vigorously for 2-3 minutes.

The formulations in Table 17 are applied to HMS according to Example 1, and the flux of ropivacaine was measured. The results are summarized in Table 18:

TABLE 18

Steady-state flux of ropivacaine HCl through hairless mouse skin from various adhesive solidifying formulations at 35° C.

| Formulation | Average flux mcg/cm²/h* |
|---|---|
| 23 | 96 ± 14 |
| 24 | 61 ± 2 |
| 25 | 70 ± 7 |

While the invention has been described with reference to certain preferred embodiments, those skilled in the art will appreciate that various modifications, changes, omissions, and substitutions can be made without departing from the spirit of the invention. It is therefore intended that the invention be limited only by the scope of the appended claims.

What is claimed is:

1. A formulation for treating neuropathic pain, comprising:
   a) at least one drug selected from the group consisting of ropivacaine, acyclovir, valacyclovir, pencyclovir, lidocaine, tetracaine, amitriptyline, ketamine, and combinations thereof;
   b) a solvent vehicle, comprising:
      i) a volatile solvent system including at least one volatile solvent, wherein volatile solvent system comprises about 10 wt % to about 85 wt % of the formulation, and
      ii) a non-volatile solvent system including at least one non-volatile solvent, wherein the non-volatile solvent system is flux-enabling for the drug and facilitates transdermal delivery of the drug at a therapeutically effective rate over a sustained period of time; and
   c) a peel-forming agent,
   wherein the formulation has a viscosity suitable for application and adhesion to a skin surface prior to evaporation of the volatile solvent system, wherein the formulation applied to the skin surface forms a solidified layer after at least partial evaporation of the volatile solvent system within about 15 minutes of application to the skin surface under standard skin and ambient conditions, and wherein the drug continues to be dermally delivered at the therapeutically effective rate after the volatile solvent system is evaporated.

2. A formulation as in claim 1, wherein the non-volatile solvent system acts as a plasticizer for the peel-forming agent.

3. A formulation as in claim 1, wherein the formulation further comprises a pH modifying agent.

4. A formulation as in claim 1, wherein the volatile solvent system comprises water.

5. A formulation as in claim 1, wherein the volatile solvent system is substantially free of water.

6. A formulation as in claim 1, wherein the volatile solvent system comprises at least one member selected from the group of ethanol, isopropyl alcohol, and combinations thereof.

7. A formulation as in claim 1, wherein the volatile solvent system comprises water and/or at least one solvent more volatile than water selected from the group consisting of ethanol, isopropyl alcohol, dimethyl ether, diethyl ether, butane, propane, isobutene, 1,1-difluoroethane, 1,1,1,2-tetrafluoroethane, 1,1,1,2,3,3,3-heptafluoropropane, 1,1,1,3,3,3-hexafluoropropane, ethyl acetate, acetone, and combinations thereof.

8. A formulation as in claim 1, wherein the volatile solvent system comprises at least one solvent more volatile than water, and includes a member selected from the group consisting of denatured alcohol, methanol, propanol, isobutene, pentane, hexane, cyclomethicone, methyl ethyl ketone, and combinations thereof.

9. A formulation as in claim 1, wherein the non-volatile solvent system comprises at least one solvent selected from the group consisting of tetrahydroxypropyl ethylenediamine, triacetin, span 20, isostearic acid, glycerol, propylene glycol, dipropylene glycol, and combinations thereof.

10. A formulation as in claim 1, wherein the non-volatile solvent system comprises at least one solvent selected from the group consisting of glycerol, propylene glycol, isostearic acid, oleic acid, propylene glycol, trolamine, tromethamine, triacetin, sorbitan monolaurate, sorbitan monooleate, sorbitan monopalmitate, and combinations thereof.

11. A formulation as in claim 1, wherein the non-volatile solvent system comprises at least one solvent selected from the group consisting of benzoic acid, dibutyl sebecate, diglycerides, dipropylene glycol, eugenol, fatty acids, isopropyl myristate, mineral oil, oleyl alcohol, vitamin E, triglycerides, sorbitan fatty acid surfactants, triethyl citrate, and combinations thereof.

12. A formulation as in claim 1, wherein the non-volatile solvent system comprises at least one solvent selected from the group consisting of 1,2,6-hexanetriol, alkyltriols, alkyldiols, tocopherol, p-propenylanisole, anise oil, apricot oil, dimethyl isosorbide, alkyl glucoside, benzyl alcohol, bees wax, benzyl benzoate, butylene glycol, caprylic/capric triglyceride, caramel, cassia oil, castor oil, cinnamaldehyde, cinnamon oil, clove oil, coconut oil, cocoa butter, cocoglycerides, coriander oil, corn oil, corn syrup, cottonseed oil, cresol, diacetin, diacetylated monoglycerides, diethanolamine, diglycerides, ethylene glycol, eucalyptus oil, fat, fatty alcohols, flavors, liquid sugars, ginger extract, glycerol, high fructose corn syrup, hydrogenated castor oil, IP palmitate, lemon oil, lime oil, limonene, monoacetin, monoglycerides, nutmeg oil, octyldodecanol, orange oil, palm oil, peanut oil, PEG vegetable oil, peppermint oil, petrolatum, phenol, pine needle oil, polypropylene glycol, sesame oil, spearmint oil, soybean oil, vegetable oil, vegetable shortening, wax, 2-(2-(octadecyloxy)ethoxy)ethanol, benzyl benzoate, butylated hydroxyanisole, candelilla wax, carnauba wax, ceteareth-20, cetyl alcohol, polyglyceryl, dipolyhydroxy stearate, PEG-7 hydrogenated castor oil, diethyl phthalate, diethyl sebacate, dimethicone, dimethyl phthalate, PEG fatty acid esters, PEG-stearate, PEG-oleate, PEG laurate, PEG fatty acid diesters, PEG- dioleate, PEG-distearate, PEG-castor oil, glyceryl behenate, PEG glycerol fatty acid esters, PEG glyceryl laurate, PEG glyceryl stearate, PEG glyceryl oleate, lanolin, lauric diethanolamide, lauryl lactate, lauryl sulfate, medronic acid, multisterol extract, myristyl alcohol, neutral oil, PEG-octyl phenyl ether, PEG-alkyl ethers, PEG-cetyl ether, PEG-stearyl ether, PEG-sorbitan fatty acid esters, PEG-sorbitan diisosterate, PEG-sorbitan monostearate, propylene glycol fatty acid esters, propylene glycol stearate, propylene glycol, caprylate/caprate, sodium pyrrolidone carboxylate, sorbitol, squalene, triglycerides, alkyl aryl polyether alcohols, polyoxyethylene derivatives of sorbitan-ethers, saturated polyglycolyzed C8-C10 glycerides, N-methyl pyrrolidone, honey, polyoxyethylated glycerides, dimethyl sulfoxide, azone and related compounds, dimethylformamide, N-methyl formamide, fatty acid esters, fatty alcohol ethers, alkyl-amides, N-methyl pyrrolidone related compounds, ethyl oleate, polyglycerized fatty acids, glycerol monooleate, glyceryl monomyristate, glycerol esters of fatty acids, silk amino acids, PPG-3 benzyl ether myristate, Di-PPG2 myreth 10-adipate, honeyquat, sodium pyroglutamic acid, abyssinica oil, dimethicone, macadamia nut oil, lirnnanthes alba seed oil, cetearyl alcohol, PEG-50, shea butter, aloe vera juice, phenyl trimethicone, hydrolyzed wheat protein, and combinations thereof.

13. A formulation as in claim 1, wherein the peel-forming agent includes at least one member selected from the group consisting of polyvinyl alcohol, esters of polyvinylmethylether/maleic anhydride copolymer, neutral copolymers of butyl methacrylate and methyl methacrylate, dimethylaminoethyl methacrylate-butyl methacrylate-methyl methacrylate copolymers, ethyl acrylate-methyl methacrylate-trimethylammonioethyl methacrylate chloride copolymers, prolamine, pregelatinized starch, ethyl cellulose, fish gelatin, gelatin, acrylates/octylacrylamide copolymers, and combinations thereof.

14. A formulation as in claim 1, wherein the peel-forming agent includes at least one member selected from the group consisting of ethyl cellulose, hydroxy ethyl cellulose, hydroxy methyl cellulose, hydroxy propyl cellulose, hydroxypropyl methyl cellulose, carboxymethyl cellulose, methyl cellulose, polyether amides, corn starch, pregelatinized corn starch, polyether amides, shellac, polyvinyl pyrrolidone, polyisobutylene rubber, polyvinyl acetate phthalate, and combinations thereof.

15. A formulation as in claim 1, wherein the peel-forming agent includes at least one member selected from the group consisting of ammonia methacrylate, carrageenan, cellulose acetate phthalate aqueous, carboxy polymethylene, cellulose acetate, cellulose polymers, divinyl benzene styrene, ethylene vinyl acetate, silicone, guar gum, guar rosin, gluten, casein, calcium caseinate, ammonium caseinate, sodium caseinate, potassium caseinate, methyl acrylate, microcrystalline wax, polyvinyl acetate, PVP ethyl cellulose, acrylate, PEG/PVP, xantham gum, trimethyl siloxysilicate, maleic acid/anhydride copolymers, polacrilin, poloxamer, polyethylene oxide, poly glactic acid/poly-l-lactic acid, turpene resin, locust bean gum, acrylic copolymers, polyurethane dispersions, dextrin, polyvinyl alcohol-polyethylene glycol co-polymers, methacrylic acid-ethyl acrylate copolymers, methacrylic acid and methacrylate based polymers, and combinations thereof.

16. A formulation as in claim 1, wherein the drug includes multiple pharmaceutically active agents.

17. A formulation as in claim 1, wherein the drug includes at least one local anesthetic selected from the group consisting of lidocaine, ropivacaine, tetracaine, and combinations thereof.

18. A formulation as in claim 17, wherein the at least one local anesthetic is in free base form.

19. A formulation as in claim 1, wherein drug is a tricyclic anti-depressant selected from the group consisting of amitriptyline, ketamine, and combinations thereof.

20. A formulation as in claim 1, wherein drug includes an antiviral drug, and the antiviral drug includes at least one member selected from the group consisting of acyclovir, penciolovir, and valacyclovir.

21. A formulation as in claim 1, wherein the solidified layer is flexible and adhesive to the skin such that when applied to the skin at a human joint, at least 70% of the solidified layer will remain intact on the skin upon bending of the joint.

22. A formulation as in claim 1, wherein the volatile solvent system comprises a volatile solvent whose boiling point is below 20° C.

23. A formulation as in claim 22, wherein the volatile solvent with the boiling point below 20° C. is completely dissolved in the formulation.

24. A formulation as in claim 22, wherein the volatile solvent with the boiling point below 20° C. is included in the formulation as a propellant for pressurized spray-on application.

25. A formulation as in claim 22, wherein the volatile solvent with the boiling point below 20° C. is a hydrofluorocarbon.

26. The formulation as in claim 22, wherein the volatile solvent whose boiling point is below 20° C. is selected from the group consisting of dimethyl ether, butane, 1,1-difluoroethane, 1,1,1,2-tetrafluoroethane, 1,1,1,2,3,3,3-heptafluoropropane, 1,1,1,3,3,3-hexafluoropropane, and combinations thereof.

27. A formulation as in claim 1, wherein the formulation is formulated to deliver the drug at therapeutically effective rates for at least about 2 hours following the formation of the solidified layer.

28. A formulation as in claim 1, wherein the formulation is formulated to deliver the drug at therapeutically effective rates for at least about 4 hours following the formation of the solidified layer.

29. A formulation as in claim 1, wherein the formulation is formulated to deliver the drug at therapeutically effective rates for at least about 8 hours following the formation of the solidified layer.

30. A formulation as in claim 1, wherein the formulation is formulated to deliver the drug at therapeutically effective rates for at least about 12 hours following the formation of the solidified layer.

31. A formulation as in claim 1, wherein the peel-forming agent is dispersed in the solvent vehicle.

32. A formulation as in claim 1, wherein peel-forming agent is solvated in the solvent vehicle.

33. A formulation as in claim 1, wherein the non-volatile solvent system is capable of causing human skin irritation and at least one non-volatile solvent of the non-volatile solvent system is capable of reducing the skin irritation.

34. A formulation as in claim 33, wherein the non-volatile solvent capable of reducing skin irritation includes member selected from the group consisting of glycerol, propylene glycol, honey, and combinations thereof.

35. A formulation as in claim 1, wherein the solidified layer is formed within about 5 minutes of the application to the skin surface under standard skin and ambient conditions.

36. A formulation as in claim 1, wherein the formulation has an initial viscosity prior to skin application from about 100 to about 3,000,000 centipoises.

37. A formulation as in claim 1, wherein the formulation has an initial viscosity prior to skin application from about 1,000 to about 1,000,000 centipoises.

38. A formulation as in claim 1, wherein the weight percentage of the volatile solvent system is from about 20 wt % to about 50 wt %.

39. A formulation as in claim 1, wherein the non-volatile solvent system includes multiple non-volatile solvents, and at least one of the non-volatile solvents is capable of improving the compatibility of the non-volatile solvent system with the peel-forming agent.

40. A formulation as in claim 1, wherein the drug is a local anesthetic agent and the non-volatile solvent system is capable of generating a flux of the local anesthetic of at least 5 mcg/cm$^2$/h.

41. A formulation as in claim 1, wherein the drug is an antiviral agent and the non-volatile solvent system is capable of generating a flux of the antiviral agent of at least 2 mcg/cm$^2$/h.

42. A formulation as in claim 1, wherein the drug is amitriptyline and the non-volatile solvent system is capable of generating a flux of the amitriptyline of at least 1 mcg/cm²/h.

43. A formulation as in claim 1, wherein the drug is ketamine and the non-volatile solvent system is capable of generating a flux of the ketamine of at least 1 mcg/cm²/h.

44. A formulation as in claim 1, wherein the solidified layer, upon formation, is a soft, coherent solid that is peelable from a skin surface as a single piece or as only a few large pieces relative to the application size.

45. A formulation as in claim 1, wherein the solidified layer transdermally delivers the drug.

46. A formulation for treating neuropathic pain, comprising:
   a) ropivacaine;
   b) a solvent vehicle, comprising:
      i) a volatile solvent system including at least one volatile solvent, and
      ii) a non-volatile solvent system including at least one solvent selected from the group consisting of an amine base, triacetin, span 20, and isostearic acid;
   c) a solidifying agent
   wherein the ropivacaine is in either base or salt form, wherein the formulation has a viscosity suitable for application to a skin surface prior to evaporation of the volatile solvent system, wherein the formulation applied to the skin surface forms a solidified, coherent, flexible, and continuous layer after at least partial evaporation of the volatile solvent system, and wherein the ropivacaine continues to be delivered at a therapeutically effective rate after the volatile solvent system is at least substantially all evaporated.

47. A formulation for treating neuropathic pain associated with a viral infection, comprising:
   a) a drug including a member selected from the group consisting of acyclovir, valacyclovir, pencyclovir, and combinations thereof;
   b) a solvent vehicle, comprising:
      i) a volatile solvent system including at least one volatile solvent, and
      ii) a non-volatile solvent system comprising at least one solvent selected from the group of oleic acid, isostearic acid, and olive oil;
   c) a solidifying agent;
   wherein the formulation has a viscosity suitable for application to a skin surface prior to evaporation of the volatile solvent system, wherein the formulation applied to the skin surface forms a solidified, coherent, flexible and continuous layer after at least partial evaporation of the volatile solvent system, and wherein the drug continues to be delivered at a therapeutically effective rate after the volatile solvent system is at least substantially all evaporated.

48. A formulation for treating neuropathic pain, comprising:
   a) a local anesthetic selected from the group consisting of lidocaine, tetracaine, and a combination thereof;
   b) a solvent vehicle, comprising:
      i) a volatile solvent system including at least one volatile solvent, and
      ii) a non-volatile solvent system including at least one solvent selected from the group consisting of propylene glycol and dipropylene glycol; and
   c) a solidifying agent,
   wherein the local anesthetic is in either base or salt form, wherein the formulation has a viscosity suitable for application to a skin surface prior to evaporation of the volatile solvent system, wherein the formulation applied to the skin surface forms a solidified, coherent, flexible and continuous layer after at least partial evaporation of the volatile solvent system, and wherein the local anesthetic continues to be delivered at a therapeutically effective rate after the volatile solvent system is at least substantially all evaporated.

49. A formulation as in claim 48, wherein the local anesthetic is lidocaine.

50. A formulation as in claim 48, wherein the local anesthetic is tetracaine.

51. A formulation as in claim 48, wherein the local anesthetic is a combination of lidocaine and tetracaine.

52. A formulation as in claim 48, wherein the local anesthetic is in base form.

53. A formulation as in claim 48, wherein the local anesthetic is in salt form.

54. A formulation for treating neuropathic pain, comprising:
   a) a drug selected from the group consisting of amitriptyline, ketamine, and combinations thereof;
   b) a solvent vehicle, comprising:
      i) a volatile solvent system including at least one volatile solvent, and
      ii) a non-volatile solvent system comprising at least one non-volatile solvent; and
   c) a solidifying agent,
   wherein the formulation has a viscosity suitable for application to a skin surface prior to evaporation of the volatile solvent system, wherein the formulation applied to the skin surface forms a solidified, coherent, flexible and continuous layer after at least partial evaporation of the volatile solvent system, and wherein the drug continues to be delivered at a therapeutically effective rate after the volatile solvent system is at least substantially all evaporated.

55. A formulation as in claim 54, wherein the drug is amitriptyline.

56. A formulation as in claim 54, wherein the drug is ketamine.

57. A formulation as in claim 54, wherein the drug is a combination of amitriptyline and ketamine.

58. A formulation for treating neuropathic pain, comprising:
   a) a drug selected from the group consisting of lidocaine, tetracaine, ropivacaine, amitriptyline, ketamine, and combinations thereof;
   b) a solvent vehicle, comprising:
      i) a volatile solvent system comprising a volatile solvent whose boiling point is below 20° C., and
      ii) a non-volatile solvent system comprising at least one non-volatile solvent; and
   c) a solidifying agent,
   wherein the formulation has a viscosity suitable for application to a skin surface prior to evaporation of the volatile solvent system, wherein the formulation applied to the skin surface forms a solidified, coherent, flexible and continuous layer after at least partial evaporation of the volatile solvent system, and wherein the drug continues to be delivered at a therapeutically effective rate after the volatile solvent system is at least substantially all evaporated.

59. A formulation as in claim 1, further comprising an additional agent that increases adhesion of the formulation when applied to a body surface.

60. A formulation as in claim 59, wherein the additional agent includes a member selected from the group consisting of copolymers of methylvinyl ether and maleic anhydride, polyethylene glycol and polyvinyl pyrrolidone, gelatin, low molecular weight polyisobutylene rubber, copolymer of acrylsan alkyl/octylacrylamido, aliphatic resins, aromatic resins, and combinations thereof.

61. A method for treating neuropathic pain, comprising:
a) applying the formulation according to claim 1
b) solidifying the formulation to form a solidified coherent, flexible, and continuous layer on the skin surface by at least partial evaporation of the volatile solvent system; and
c) dermally delivering the drug from the solidified layer to the subject at therapeutically effective rates over a sustained period of time to reduce the neuropathic pain, wherein the drug continues to be delivered at a therapeutically effective rate after the volatile solvent system is at least substantially all evaporated.

62. A method as in claim 61, wherein the step of applying includes applying the formulation at a thickness from about 0.01 mm to about 3 mm.

63. A method as in claim 61, wherein the step of applying includes applying the formulation at a thickness from about 0.05 mm to about 1 mm.

64. A method as in claim 61, wherein the volatile solvent system comprises water.

65. A method as in claim 61, wherein the volatile solvent system comprises ethanol, propanol, or a combination thereof.

66. A method as in claim 61, wherein the volatile solvent system includes at least one member selected from the group consisting of ethanol, isopropyl alcohol, water, dimethyl ether, diethyl ether, butane, propane, isobutene, 1,1-difluoroethane, 1,1,1,2-tetrafluoroethane, 1,1,1,2,3,3,3-heptafluoropropane, 1,1,1,3,3,3-hexafluoropropane, ethyl acetate, acetone and combinations thereof.

67. A method as in claim 61, wherein the volatile solvent system includes at least one member selected from the group consisting of denatured alcohol, methanol, propanol, isobutene, pentane, hexane, cyclomethicone, methyl ethyl ketone, and combinations thereof.

68. A method as in claim 61, wherein the non-volatile solvent system comprises at least one solvent including a member selected from the group consisting of tetrahydroxypropyl ethylenediamine, triacetin, span 20, isostearic acid, glycerin, propylene glycol, dipropylene glycol, or a mixture thereof.

69. A method as in claim 61, wherein the non-volatile solvent system includes at least one member selected from the group consisting of glycerol, propylene glycol, isostearic acid, oleic acid, trolamine, tromethamine, triacetin, sorbitan monolaurate, sorbitan monooleate, sorbitan monopalmitate, and combinations thereof.

70. A method as in claim 61, wherein the non-volatile solvent system includes at least one member selected from the group consisting of benzoic acid, dibutyl sebecate, diglycerides, dipropylene glycol, eugenol, fatty acids, isopropyl myristate, mineral oil, oleyl alcohol, vitamin E, triglycerides, sorbitan fatty acid surfactants, triethyl citrate, and combinations thereof.

71. A method as in claim 61, wherein the non-volatile solvent system includes at least one member selected from the group consisting of 1,2,6-hexanetriol, alkyltriols, alkyldiols, tocopherol, p-propenylanisole, anise oil, apricot oil, dimethyl isosorbide, alkyl glucoside, benzyl alcohol, bees wax, benzyl benzoate, butylene glycol, caprylic/capric triglyceride, caramel, cassia oil, castor oil, cinnamaldehyde, cinnamon oil, clove oil, coconut oil, cocoa butter, cocoglycerides, coriander oil, corn oil, corn syrup, cottonseed oil, cresol, diacetin, diacetylated monoglycerides, diethanolamine, diglycerides, ethylene glycol, eucalyptus oil, fat, fatty alcohols, flavors, liquid sugars, ginger extract, glycerin, high fructose corn syrup, hydrogenated castor oil, IP palmitate, lemon oil, lime oil, limonene, monoacetin, monoglycerides, nutmeg oil, octyldodecanol, orange oil, palm oil, peanut oil, PEG vegetable oil, peppermint oil, petrolatum, phenol, pine needle oil, polypropylene glycol, sesame oil, spearmint oil, soybean oil, vegetable oil, vegetable shortening, wax, 2-(2-(octadecyloxy)ethoxy)ethanol, benzyl benzoate, butylated hydroxyanisole, candelilla wax, carnauba wax, ceteareth-20, cetyl alcohol, polyglyceryl, dipolyhydroxy stearate, PEG-7 hydrogenated castor oil, diethyl phthalate, diethyl sebacate, dimethicone, dimethyl phthalate, PEG fatty acid esters, PEG-stearate, PEG-oleate, PEG laurate, PEG fatty acid diesters, PEG- dioleate, PEG-distearate, PEG-castor oil, glyceryl behenate, PEG glycerol fatty acid esters, PEG glyceryl laurate, PEG glyceryl stearate, PEG glyceryl oleate, lanolin, lauric diethanolamide, lauryl lactate, lauryl sulfate, medronic acid, multisterol extract, myristyl alcohol, neutral oil, PEG-octyl phenyl ether, PEG-alkyl ethers, PEG-cetyl ether, PEG-stearyl ether, PEG-sorbitan fatty acid esters, PEG-sorbitan diisosterate, PEG-sorbitan monostearate, propylene glycol fatty acid esters, propylene glycol stearate, propylene glycol, caprylate/caprate, sodium pyrrolidone carboxylate, sorbitol, squalene, stear-o-wet, triglycerides, alkyl aryl polyether alcohols, polyoxyethylene derivatives of sorbitan-ethers, saturated polyglycolyzed C8-C10 glycerides, N-methyl pyrrolidone, honey, polyoxyethylated glycerides, dimethyl sulfoxide, azone and related compounds, dimethylformamide, N-methyl formamide, fatty acid esters, fatty alcohol ethers, alkyl-amides (N,N-dimethylalkylamides), N-methyl pyrrolidone related compounds, ethyl oleate, polyglycerized fatty acids, glycerol monooleate, glyceryl monomyristate, glycerol esters of fatty acids, silk amino acids, PPG-3 benzyl ether myristate, Di-PPG2 myreth 10-adipate, honeyquat, sodium pyroglutamic acid, abyssinica oil, dimethicone, macadamia nut oil, limnanthes alba seed oil, cetearyl alcohol, PEG-50 shea butter, shea butter, aloe vera juice, phenyl trimethicone, hydrolyzed wheat protein, and combinations thereof.

72. A method as in claim 61, wherein the peel-forming agent includes at least one member selected from the group consisting of polyvinyl alcohol, esters of polyvinylmethylether/maleic anhydride copolymer, neutral copolymers of butyl methacrylate and methyl methacrylate, dimethylaminoethyl methacrylate-butyl methacrylate-methyl methacrylate copolymers, ethyl acrylate-methyl methacrylate-trimethylammonioethyl methacrylate chloride copolymers, prolamine, pregelatinized starch, ethyl cellulose, fish gelatin, gelatin, acrylates/octylacrylamide copolymers, and combinations thereof.

73. A method as in claim 61, wherein the peel-forming agent includes at least one member selected from the group consisting of ethyl cellulose, hydroxy ethyl cellulose, hydroxy methyl cellulose, hydroxy propyl cellulose, hydroxypropyl methyl cellulose, carboxymethyl cellulose, methyl cellulose, polyether amides, corn starch, pregelatinized corn starch, polyether amides, shellac, polyvinyl pyrrolidone, polyisobutylene rubber, polyvinyl acetate phthalate and combinations thereof.

74. A method as in claim 61, wherein the peel-forming agent includes at least one member selected from the group consisting of ammonia methacrylate, carrageenan, cellulose acetate phthalate aqueous, carboxy polymethylene, cellulose acetate, cellulose polymers, divinyl benzene styrene, ethylene vinyl acetate, silicone, guar gum, guar rosin, gluten, casein, calcium caseinate, ammonium caseinate, sodium caseinate, potassium caseinate, methyl acrylate, microcrystalline wax, polyvinyl acetate, PVP ethyl cellulose, acrylate, PEG/PVP, xantham gum, trimethyl siloxysilicate, maleic acid/anhydride copolymers, polacrilin, poloxamer, polyethylene oxide, poly glactic acid/poly-l-lactic acid, turpene resin, locust bean gum, acrylic copolymers, polyurethane dispersions, dextrin, polyvinyl alcohol-polyethylene glycol co-polymers, methyacrylic acid-ethyl acrylate copolymers, methacrylic acid and methacrylate based polymers, and combinations thereof.

75. A method as in claim 61, wherein the drug includes multiple pharmaceutically active agents.

76. A method as in claim 61, wherein the solidified layer is sufficiently flexible and adhesive to the skin such that when applied to the skin at a human joint, the solidified layer will remain substantially intact on the skin upon bending of the joint.

77. A method as in claim 61, wherein the formulation is left on the skin for at least about 2 hours following the formation of the solidified layer.

78. A method as in claim 61, wherein the formulation is left on the skin for at least about 8 hours following the formation of the solidified layer.

79. A method as in claim 61, wherein the weight ratio of the non-volatile solvent system to the solidifying agent is from about 0.5:1 to about 2:1.

80. A method as in claim 61, wherein the solidified layer is formed within 15 minutes of application to the skin surface under standard skin and ambient conditions.

81. A method as in claim 61, wherein the formulation is sprayed on the skin.

82. A method as in claim 61, wherein the formulation is applied on the skin using a manual pump.

83. A method as in claim 61, wherein the formulation has an initial viscosity prior to skin application from about 100 to about 3,000,000 centipoises.

84. A method as in claim 61, wherein the drug is a local anesthetic agent and the non-volatile solvent system is capable of generating a flux of the local anesthetic of at least 5 mcg/cm$^2$/h.

85. A method as in claim 61, wherein the drug is an antiviral agent and the non-volatile solvent system is capable of generating a flux of the antiviral agent of at least 2 mcg/cm$^2$/h.

86. A method as in claim 61, wherein the drug is ketamine and the non-volatile solvent system is capable of generating a flux of the ketamine of at least 1 mcg/cm$^2$/h.

87. A method as in claim 61, wherein the drug is amitriptyline and the non-volatile solvent system is capable of generating a flux of the amitriptyline of at least 1 mcg/cm$^2$/h.

88. A method as in claim 61, further comprising the step of peeling the solidified layer from the skin after the sustained period of time to remove the solidified layer.

89. A method as in claim 61, further comprising the step of washing the solidified layer form the skin using a solvent after the sustained period of time to remove the solidified layer.

90. A method as in claim 61, wherein the neuropathic pain is associated with shingles.

91. A method as in claim 61, wherein the neuropathic pain is associated with diabetes.

92. A method as in claim 61, wherein the neuropathic pain is associated with postherpatic neuralgia.

93. A method as in claim 61, wherein the neuropathic pain is associated with postsurgical or post-traumatic pain.

* * * * *